United States Patent [19]

Felgner et al.

[11] Patent Number: 5,264,618
[45] Date of Patent: Nov. 23, 1993

[54] CATIONIC LIPIDS FOR INTRACELLULAR DELIVERY OF BIOLOGICALLY ACTIVE MOLECULES

[75] Inventors: Philip L. Felgner, Rancho Santa Fe; Raj Kumar; Channa Basava, both of San Diego; Richard C. Border, Poway; Jiin-Yu Hwang-Felgner, Rancho Santa Fe, all of Calif.

[73] Assignee: Vical, Inc., San Diego, Calif.

[21] Appl. No.: 686,746

[22] Filed: Apr. 16, 1991

Related U.S. Application Data

[63] Continuation of Ser. No. 563,444, Aug. 7, 1990, abandoned, which is a continuation of Ser. No. 511,219, Apr. 19, 1990, abandoned.

[51] Int. Cl.$^5$ ............................................. C07C 69/52
[52] U.S. Cl. ................... 560/224; 560/155; 560/252; 530/323; 554/227; 554/224; 554/223; 564/292; 574/549; 574/552
[58] Field of Search ............... 560/224; 554/227, 226, 554/223; 530/323; 574/292, 549, 552

[56] References Cited

U.S. PATENT DOCUMENTS 3,931,397 7/1976 Harnden ................................ 424/85
4,897,355 3/1990 Eppstein et al. ..................... 424/427

FOREIGN PATENT DOCUMENTS 0187702 1/1986 .
3102682 7/1988 Japan .

OTHER PUBLICATIONS

CA 112(2):86804 1988.
CA 107(25):236676d 1987.
Duzgunes, N., *Subcellular Biochemistry* 11:195–286 (1985).
Mannino, R. J., et al. *Biotechniques* 6:682–690 (1988).
Itani, T., et al. *Gene* 56:267–276 (1987).
Nicolau, C., et al. *Meth. Enz.* 149:157–176 (1987).
Straubinger, R., et al. *Meth. Enz.* 101:512–527 (1983).
Felgner, P., et al., *Proc. Natl. Acad. Sci. USA* 84:7413–7417 (1987).
Ballas, N., et al., *Biochim. Biophys. Acta* 939:8–18 (1988).
Pinnaduwage, P., et al., *Biochim. Biophys. Acta* 985:33–37 (1989).
Behr, J.-P., et al., *Proc. Natl. Acad. Sci. USA* 86:6982–6986 (1989).
Eibl, H., et al., *Biophys. Chem.* 10:261–271 (1979).
Stamatotos, L., et al. *Biochemistry* 27:3917–3925 (1988).
Carmona-Ribeiro, A., et al., *J. Phys. Chem.* 89:2928–2933 (1985).
Rupert, L., et al., *J. Amer. Chem. Soc.* 108:3920–3925 (1986).

(List continued on next page.)

*Primary Examiner*—Paul J. Killos
*Attorney, Agent, or Firm*—Knobbe, Martens, Olson & Bear

[57] ABSTRACT

Disclosed are cationic lipids capable of facilitating transport of biologically active agents into cells, including the transfection of cells by therapeutic polynucleotides, the delivery of antiviral drugs, and the introduction of immunogenic peptides. The cationic lipids, comprising an ammonium group, have the general structure

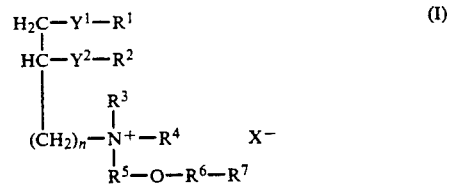

Also disclosed are adducts of these compounds comprising additional cationic sites that enhance the transfective or transport activity. Structure-activity correlations provide for the selection of preferred compounds to be synthesized for this purpose. Compositions disclosed for use of these cationic lipid include formulations for in vitro transfection and pharmaceutical formulations for parenteral and topical administration of therapeutic agents.

12 Claims, 18 Drawing Sheets

OTHER PUBLICATIONS

Rosenthal, A., et al., *J. Biol. Chem.* 235(8):2202–2206 (1960).
Wilschut, J., et al., *Biochemistry* 199:6011–6021 (1980).
Mayer, L., et al., *Biochim. Biophys. Acta* 858:161–168 (1986).
Bangham, A., et al., *J. Mol. Biol.* 23:238–252 (1965).
Olson, F., et al., *Biochim. Biophys. Acta* 557:9–23 (1979).
Szoka F., et al., *Proc. Natl. Acad. Sci. USA* 75:4194–4198 (1978).
Mayhew E., et al. *Biochim. Biophys. Acta* 775:169–175 (1984).
Kim, S., et al. *Biochim. Biophys. Acta* 728:339–348 (1983).
Fukunaga M., et al., *Endrocrinol.* 115:757–761 (1984).
Israelachvili, J., et al., *Biochim. Biophys. Acta* 470:185–201 (1977).
Kunkel, L., et al. *Brit. Med. Bull.* 45(3):630–643 (1989).
Goodfellow, P. *Nature* 341(6238): 102–3 (Sep. 14, 1989).
Ts'o P., et al., *Annals New York Acad. Sci.* 570:220–241 (1987).
Hampel, et al., *Nucleic Acids Research* 18(2): 299–304 (1990).
Cech, T., et al., *Annual Rev. Biochem.* 55:5499–629 (1986).
Matsukura, M., et al., *Proc. Nat'l Acad. Sci.* 86:4244–4248 (1989).
Kumar, R., et al., *Biochim. Biophys. Acta* 917:33–41 (1987).
Brigham, K., et al. *Amer. J. of the Med. Sci.* 298(4):278–281 (1989).
Berge, S., et al., *J. of Pharmaceutical Sciences* 66:1–19 (1977).
Felgner, P., et al., *Focus* 11(2): (Spring 1989).
Malone, R., et al., *Proc. Nat'l Acad. Sci. USA* 86:6077–6081 (1989).
Chiang, M.-L., et al., J. Biol. Chem. 268:1–10 (1991).
Felgner, P., et al. *Nature* 349(6307): 351–352 (1991).
R. Elbert et al., *J. Amer. Chem. Soc.*, 107: 4134–4141 (1985).
K. L. Meyer, et al., *J. Med. Chem.*, 34: 1377–1383 (1991).

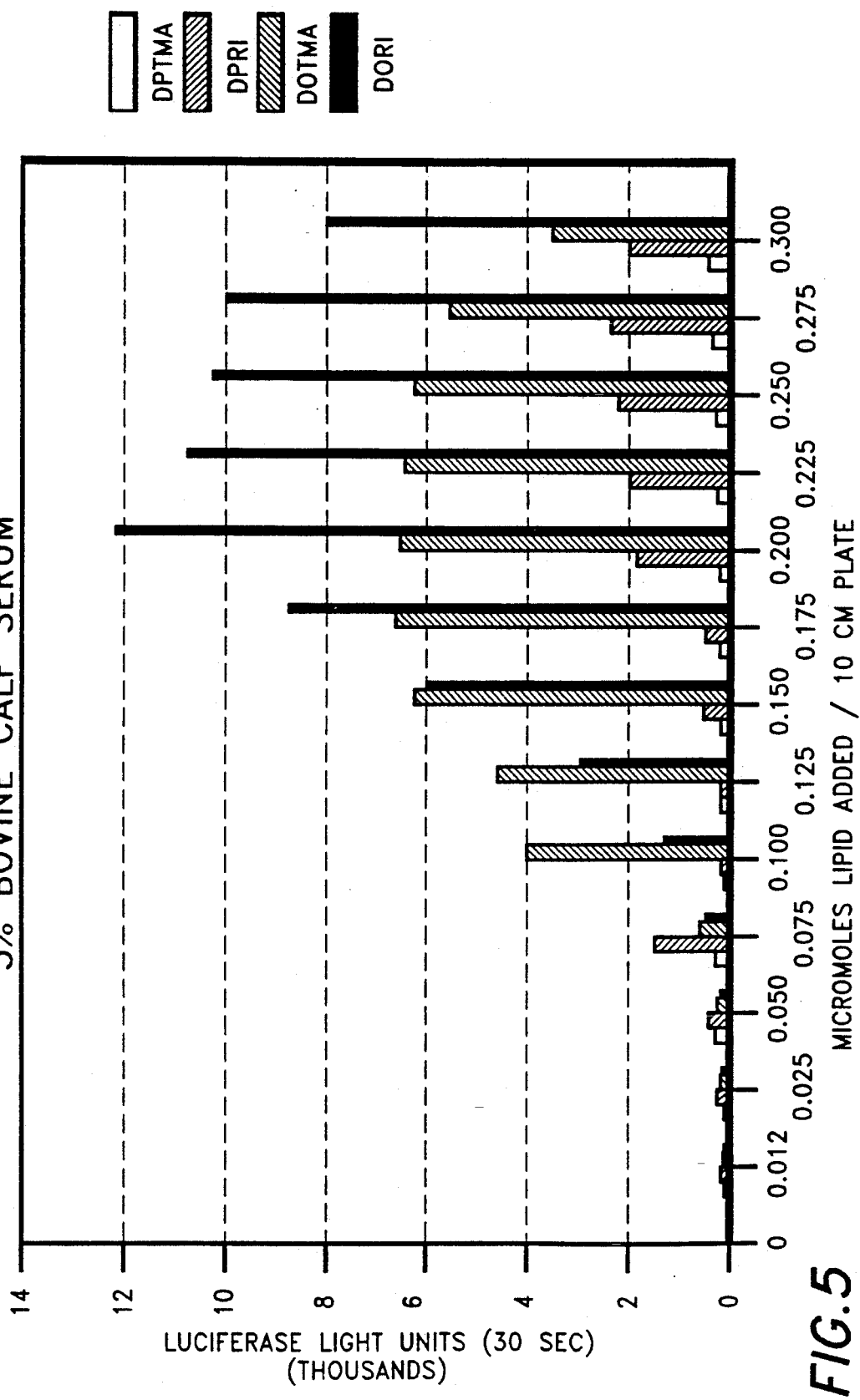

CATIONIC LIPIDS FOR INTRACELLULAR DELIVERY OF BIOLOGICALLY ACTIVE MOLECULES

This application is a continuation-in-part of U.S. applications Ser. No. 07/563,444, filed Aug. 7, 1990 abandoned; and Ser. No. 07/511,219, filed Apr. 19, 1990 abandoned.

BACKGROUND OF THE INVENTION

The present invention relates to cationic lipids which are used to enhance delivery of biologically active agents, particularly polynucleotides, proteins, peptides, and drug molecules, by facilitating transmembrane transport or by encouraging adhesion to biological surfaces. It relates particularly to cationic lipids comprising ammonium groups.

Some bioactive substances do not need to enter cells to exert their biological effect, because they operate either by acting on cell surfaces through cell surface receptors or to by interacting with extracellular components. However, many natural biological molecules and their analogues, including proteins and polynucleotides, or foreign substances, such as drugs, which are capable of influencing cell function at the subcellular or molecular level are preferably incorporated within the cell in order to produce their effect. For these agents the cell membrane presents a selective barrier which is impermeable to them.

Just as the plasma membrane of a cell is a selective barrier preventing random introduction of potentially toxic substances into the cell, the human body is surrounded by protective membranes which serve a similar defensive function to the whole organism. These membranes include skin, gastric mucosa, nasal mucosa and the like. While these membranes serve a protective function preventing entry of toxic substances, they can also prevent passage of potentially beneficial therapeutic substances into the body. The complex composition of the cell membrane comprises phospholipids, glycolipids, and cholesterol, as well as intrinsic and extrinsic proteins, and its functions are influenced by cytoplasmic components which include $Ca^{++}$ and other metal ions, anions, ATP, microfilaments, microtubules, enzymes, and $Ca^{++}$-binding proteins. Interactions among structural and cytoplasmic cell components and their response to external signals make up transport processes responsible for the membrane selectivity exhibited within and among cell types.

Successful intracellular delivery of agents not naturally taken up by cells has been achieved by exploiting the natural process of intracellular membrane fusion, or by direct access of the cell's natural transport mechanisms which include endocytosis and pinocytosis (Duzgunes, N., *Subcellular Biochemistry* 11:195-286 (1985).

The membrane barrier can be overcome in the first instance by associating these substances in complexes with lipid formulations closely resembling the lipid composition of natural cell membranes. These lipids are able to fuse with the cell membranes on contact, and in the process, the associated substances are delivered intracellularly. Lipid complexes can not only facilitate intracellular transfers by fusing with cell membranes but also by overcoming charge repulsions between the cell membrane and the molecule to be inserted. The lipids of the formulations comprise an amphipathic lipid, such as the phospholipids of cell membranes, and form hollow lipid vesicles, or liposomes, in aqueous systems. This property can be used to entrap the substance to be delivered within the liposomes; in other applications, the drug molecule of interest can be incorporated into the lipid vesicle as an intrinsic membrane component, rather than entrapped into the hollow aqueous interior.

Intracellular delivery of beneficial or interesting proteins can be achieved by introducing expressible DNA and mRNA into the cells of a mammal, a useful technique termed transfection. Gene sequences introduced in this way can produce the corresponding protein coded for by the gene by using endogenous protein synthetic enzymes. The therapy of many diseases could be enhanced by the induced intracellular production of peptides which could remain inside the target cell, be secreted into the local environment of the target cell, or be secreted into the systemic circulation to produce their effect.

Various techniques for introducing the DNA or mRNA precursors of bioactive peptides into cells include the use of viral vectors, including recombinant vectors and retroviruses, which have the inherent ability to penetrate cell membranes. However, the use of such viral agents to integrate exogenous DNA into the chromosomal material of the cell carries a risk of damage to the genome and the possibility of inducing malignant transformation. Another aspect of this approach which restricts its use in vivo is that the integration of DNA into the genome accomplished by these methods implies a loss of control over the expression of the peptide it codes for, so that transitory therapy is difficult to achieve and potential unwanted side effects of the treatment could be difficult or impossible to reverse or halt.

Liposomes have been discussed as possible in vivo delivery vehicles and some encouraging results using this approach to the intracellular expression of DNA have been obtained (Mannino, R. J. Fould-Fogerite, S., *Biotechniques* 6, 682-690 (1988); Itani, T., Ariga, H., Yamaguchi, N., Tadakuma, T. & Yasuda, T. *Gene* 56 267-276 (1987); Nicolau, C. Legrand, A. & Grosse, G. E. *Meth. Enz.* 149 157-176 (1987); Straubinger, R. M. & Papahadjopoulos, D. *Meth. Enz.* 101 512-527 (1983); Wang, C. Y. & Huang, L. *Proc Natl. Acad. Sci. USA* 84 7851-7855 (1987)); however, the methodology has fundamental problems. Chief among the difficulties is the failure of liposomes to fuse with the target cell surface, but to be taken up phagocytically instead. Phagocytized liposomes are delivered to the lysosomal compartment, where polynucleotides are subjected to the action of digestive enzymes and degraded, leading to low efficiency of expression.

A major advance in this area was the discovery that a positively charged synthetic cationic lipid, N-[1-(2,3-dioleyloxy)propyl]-N,N,N-trimethylammonium chloride (DOTMA), in the form of liposomes, or small vesicles, could interact spontaneously with DNA to form lipid-DNA complexes which are capable of fusing with the negatively charged lipids of the cell membranes of tissue culture cells, resulting in both uptake and expression of the DNA (Felgner, P. L. et al. *Proc. Natl. Acad. Sci., USA* 84:7413-7417 (1987) and U.S. Pat. No. 4,897,355 to Eppstein, D. et al.). Others have successfully used a DOTMA analogue, 1,2-bis(oleoyloxy)-3-(trimethylammonio)propane (DOTAP) in combination with a phospholipid to form DNA-complexing vesicles. The Lipofectin ™ reagent (Bethesda Research Laboratories, Gaithersburg, Md.), an effective agent for the delivery of highly anionic polynucleotides into living tissue culture cells comprises positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional polynucleotide into, for example, tissue culture cells.

Although the use of known cationic lipids overcomes many problems associated with conventional liposome technology for polynucleotide delivery in vitro, several problems related to both in vitro and in vivo applications remain. First, although the efficiency of cationic lipid mediated delivery is relatively high compared to other methods, the absolute level of gene product produced is typically only several hundred copies per cell on average. Thus it would be desirable to improve delivery and expression by a factor of 10 to 1000-fold to achieve useful methodologies. Secondly, known cationic lipids such as DOTMA are toxic to tissue culture cells; thus, any improvements that reduce in vitro toxicity would strengthen the methodology.

A significant body of information is emerging regarding the use of other cationic lipids for the delivery of macromolecules into cells. Loyter prepared vesicles containing a quaternary ammonium surfactant that are capable of transferring functional tobacco mosaic virus into plant protoplasts. (Ballas, N., Zakai, N., Sela, I. and Loyter, A. *Biochim. Biophys Acta* 939 8–18 (1988)). Huang used cetyltrimethylammonium bromide to obtain functional expression from the chloramphenicol acetyl transferase gene transfected into mouse fibroblasts (Pinnaduwage, P., Schmitt, L. and Huang, L. *Biochim. Biophys Acta* 985 33–37 (1989)). Behr has shown that a novel lipophilic derivative of spermine can transfect primary pituitary cells (Behr, J-P, Demeneix, B., Loeffler, J-P and Perez-Mutul, J. *Proc. Natl. Acad. Sci. USA* 86 6982–6986 (1989)). Finally, John Silvius has shown that a cationic lipid (DOTAP), originally synthesized by Eibl (Eibl, H. and Woolley, P. *Biophys. Chem.* 10 261–271 (1979)) forms liposomes which can fuse with negatively charged liposomes and can deliver functional DNA and RNA into tissue culture fibroblasts (Stamatatos, L., Leventis, R., Zuckermann, M. J. & Silvius, J. R. *Biochemistry* 27 3917–3925 (1988)). Other laboratories have studies the physical properties of vesicles formed from synthetic cationic amphophiles (Rupert, L. A. M., Hoekstra, D. and Engberts, J. B. F. N. *Am. Chem. Soc.* 108: 2628–2631 (1985); Carmona-Ribeiro, A. M., Yoshida, L. S. and Chaimovich, H. *J. Phys Chem* 89 2928–2933 (1985); Rupert, L. A. M., Engberts, J. B. F. N. and Hoekstra, D. *J. Amer. Chem. Soc.* 108:3920–3925 (1986)).

It is not feasible to extend in vitro transfection technology to in vivo applications directly. In vivo, the diether lipids, such as DOTMA or Lipofectin the current commercial standard, would be expected to accumulate in the body due to the poorly metabolized ether bonds. And finally, it has been reported that the cationic lipid transfection methodology is inhibited by serum; for in vivo applications conditions must be identified which allow transfection to occur in a complex biological milieu such as 100% serum.

Therefore, while the known lipofection technique of transfection described is more efficient and satisfactory than previously known procedures, and permits transient as well as stable transfection and peptide expression, it is not understood what factors regulate the efficiency of the transfection process and how it may be optimized. It would be desirable to determine these factors in order to develop an intracellular delivery system having the advantages of the above-described systems but without their inherent limitations.

Accordingly, it is an object of the invention to provide cationic lipids which carry out both stable and transient transfections of polynucleotides such as DNA and mRNA into cells more effectively.

It is also an object of the invention to provide cationic lipids which deliver other molecules of therapeutic interest, including proteins, peptides and small organic molecules, into cells more effectively.

Further, it is an object of the invention to provide cationic lipids that are not only more effective in accomplishing intracellular delivery but are also metabolizable so as to have reduced in vivo and in vitro toxicity.

It is another object of the invention to provide transfection formulation, comprising novel cationic lipids, that are optimally effective in both in vivo and in vitro transfection.

BRIEF DESCRIPTION OF THE FIGURES

FIG. 5 demonstrates the comparative effectiveness of DPTMA, DOTMA and corresponding derivatives of the Rosenthal Inhibitor in RNA transfection.

SUMMARY OF THE INVENTION

Figure 1:
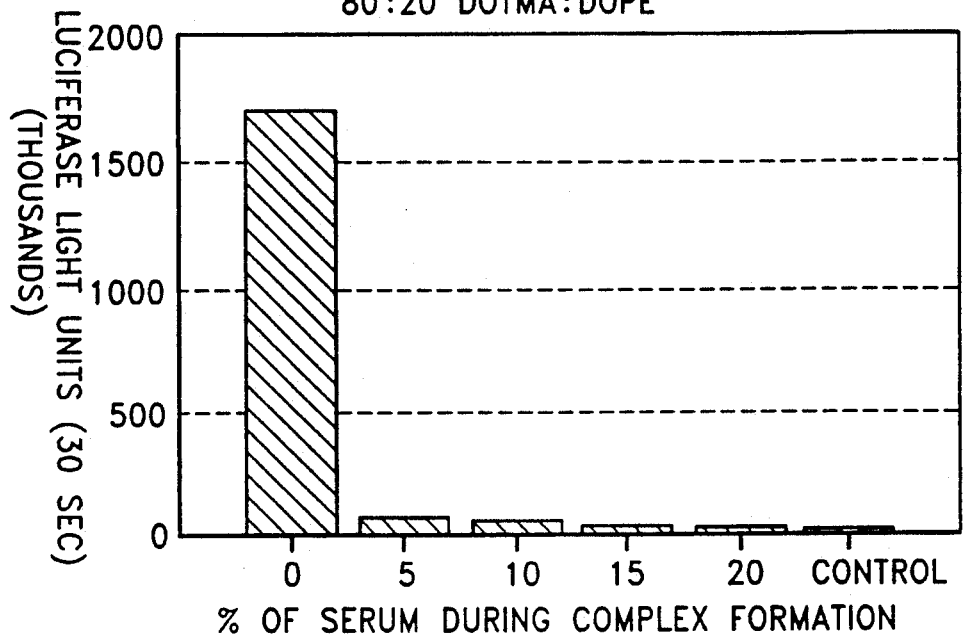
FIG. 1 presents data showing the effect the presence of serum during lipid complex formation on subsequent RNA transfection.

The present invention provides compositions of novel cationic lipids, suitable for use in the intracellular delivery of bioactive agents, comprising polynucleotides, proteins, small organic molecules and drugs, in both in vivo and in vitro applications, and into the cells of plants and animals.

These compositions have the general structure

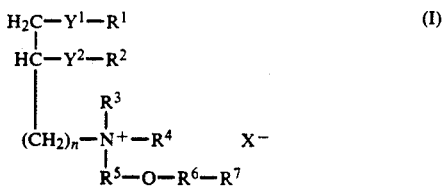

wherein $Y^1$ and $Y^2$ are the same or different and are —O—CH$_2$—, —O—C(O)—, or —O—;

$R^1$ and $R^2$ are the same or different and are H, or C$_1$ to C$_{23}$ alkyl or alkenyl; and $R^3$, $R^4$, $R^5$, $R^6$, and $R^7$ are as defined below. Preferred embodiments are compositions wherein $R^3$ and $R^4$ are individually C$_1$ to C$_{23}$ alkyl groups, $R^5$ is —(CH$_2$)$_m$—, $R^6$ is absent, $R^7$ is H, and $R^1$ and $R^2$ individually have from 0 to 6 sites of unsaturation, and have the structure

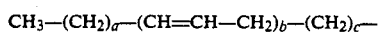

wherein the sum of a and c is from 1 to 23; and b is 0 to 6.

Particularly preferred embodiments are compositions wherein the long chain alkyl groups are fatty acids, that is, wherein $Y^1$ and $Y^2$ are alike and are —O—C(O)—. These compounds are easily metabolized by cells and therefore lack the toxicity of presently known transfection agents. A specific example of this class of compounds is DL-1,2-dioleoyl-3-dimethylaminopropyl-B-hydroxyethylammonium and its salts.

Other particularly preferred embodiments are those compounds wherein $Y^1$ and $Y^2$ are alike and are —O—CH2—. These compounds, having ether-linked alkyl groups, have been found to be superior in transfective properties to presently known cationic lipids. A specific example of a compound of this class is 1,2-O-dioleyl-3-dimethylaminopropyl-β-hydroxyethylammonium and its salts. Useful cationic lipids for intracellular delivery also comprise compounds wherein $Y^1$ and $Y^2$ are different and are either —O—CH2— or —O—C(O)—. These compounds, having alkyl groups attached by both ether and ester linkages, will have combined properties of low toxicity and improved transfective properties. A particularly preferred composition of this class is 1-O-oleyl-2-oleoyl-3-dimethylaminopropyl-β-hydroxyethylammonium and its salts.

Additional novel cationic lipids provided by the invention are adducts of the general structure comprising additional cationic groups attached at the hydroxyl of the β-hydroxyethanolamine moiety. In preferred embodiments of this class of compounds, the additional cationic groups are provided by lysyl groups attached to the hydroxyl group through a diaminocarboxylic acid linker. A glycyl spacer may connect the linker to the hydroxyl group. Particularly preferred compositions of this class are 3,5-(N,N-dilysyl)-diaminobenzoyl-3-(DL-1,2-dioleoyl-dimethylaminopropyl-β-hydroxyethylamine) and 3,5-(N,N-dilysyl)diaminobenzoylglycyl-3-(DL-1,2-dioleoyl-dimethylaminopropyl-β-hydroxyethylamine).

Alternatively, the additional cationic groups of the adduct can be provided by attaching cationic amine-containing groups such as, for example, spermine, spermidine, histones, or other molecules known to bind DNA. Preferred embodiments of this class of compositions are L-spermine-5-carboxyl-3-(DL-1,2-dioleoyl-dimethylaminopropyl-β-hydroxyethylamine). These cationic groups can in turn provide further hydrophobic regions to the cationic lipid composition through alkyl quaternizing groups on the attached lysine, spermine, or other amine-containing groups.

Also included within the scope of the invention are analogues of known cationic lipids having ester linkages substituted for ether linkages between alkyl substituents and the glycerol moiety of the structure to provide less toxic, more easily metabolized compositions suitable for use in vivo. These analogues have the general structure

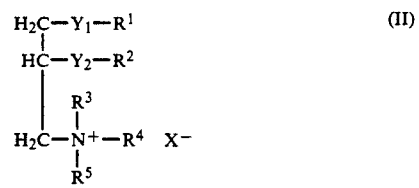

or an optical isomer thereof, wherein $Y^1$ and $Y^2$ are different and are either —O—CH2—, —O—C(O)— or —O—;

$R^1$ and $R^2$ are individually C$_1$ to C$_{23}$ alkyl or alkenyl, or H; and $R^3$, $R^4$, $R^5$ and X are as defined below.

According to yet another aspect of the invention there are provided lipid formulations for transfection comprising a cationic lipid and an effective transfection-promoting amount of a lysophosphatide, having the structure

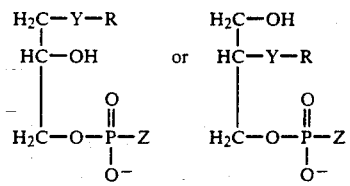

wherein Y is selected from the group consisting of —O—CH2— and —O—C(O)—;

R is C$_{10}$ to C$_{23}$ alkyl or alkenyl; and

Z is a headgroup.

Preferred formulations for transfection of polynucleotides and peptides into cells comprise novel cationic compounds of the invention having the structure set forth herein, together with an effective transfection-promoting amount of a lysophosphatide. The lysophosphatide may have a neutral or a negative headgroup. Lysophosphatidylcholine and lysophosphatidylethanolamine are preferred, and 1-oleoyl lysophosphatidylcholine is particularly preferred. Lysophosphatide lipids are advantageously present in the formulation in a molar ratio of 0.5 lyso lipid to cationic lipid.

Lyso forms of cationic lipids, selected from the novel cationic lipids of the invention, DOTMA, or DOTAP can also be used to increase the effectiveness of the transfection. These lyso forms are advantageously present in effective amounts up to about one-third of the total cationic lipid in the formulations.

According to another aspect of the invention, there is provided a liposomal formulation, comprising a cationic lipid of the invention, wherein the cationic lipid is in the form of vesicles in an aqueous media. The lipids of the liposomal formulation can further comprise a neutral lipid species selected from the group consisting of phosphatidylcholine, phosphatidylethanolamine, sphingomyelin, or cholesterol. A preferred molar ratio of cationic to neutral lipid species in these formulations is from about 9/1 to 1/9; a molar ratio of about 5/5 is particularly preferred. The liposomal formulation can further comprise a lyso lipid selected from the group consisting of lysophosphatidylcholine, lysophosphatidylethanolamine, or a lyso form of a cationic lipid species.

According to yet another aspect of the invention, there are provided pharmaceutical products comprising the cationic lipids of the invention having any of the structures disclosed herein together with a pharmacologically effective amount of a therapeutic agent. Cationic lipids present in these compositions facilitate the intracellular delivery of the active therapeutic agent. Products are provided for topical, enteral and parenteral uses. In one pharmaceutical product the therapeutic agent is a steroid; in another, the therapeutic agent is a non-steroidal anti-inflammatory agent.

In other pharmaceutical products of the invention, the therapeutic agent is an antiviral nucleoside analogue or preferably a lipid derivative of an antiviral nucleoside analogue, which is a phosphatidyl derivative, or a diphosphate diglyceride derivative. The antiviral nucleoside can be a dideoxynucleoside, a didehydronucleoside, a halogenated or azido- derivative of a nucleoside, or an acyclic nucleoside. In preferred embodiments, the lipid derivatives of antiviral nucleosides are (3'-azido-3'-deoxy)thymidine-5'-diphospho-3-diacylglycerol (AZT diphosphate diglyceride) and dideoxythymidine diphosphate diglyceride. In particularly preferred embodiments, the lipid derivative of an antiviral nucleoside is an acyclovir or gancyclovir diphosphate diglyceride or diphosphate diglyceride derivatives of 1-(2-deoxy-2'-fluoro-1-β-D-arabinofuranosyl)-5-iodocytosine (FIAC) or 1(2'-deoxy-2'-fluoro-1-β-D-arabinofuranosyl)-5-iodouracil (FIAU).

In other pharmaceutical products of the invention the therapeutic agent is a polynucleotide. In one of these embodiments, the therapeutic polynucleotide is a ribozyme, or an antisense RNA or DNA. In preferred embodiments, the formulation comprises an antisense DNA or RNA or a ribozyme directed against HIV. In a particularly preferred embodiment, the therapeutic polynucleotide is an antisense DNA or RNA or a ribozyme directed against the rev transactivator of HIV. An example of such an agent is the 28-mer phosphorothioate antisense polynucleotide. Alternatively, the therapeutic polynucleotide can be one coding for an immunogen, a natural hormone, or a synthetic analogue of a natural hormone; or it can be a polynucleotide sequence coding for a gene product that is deficient or absent in a disease state, and administration of said product to a human in need of therapy relating to said gene product has a therapeutic effect.

The pharmaceutical products disclosed may also comprise a therapeutic protein or polypeptide corresponding to those coded for by the therapeutic polynucleotides described above.

In a preferred embodiment, the invention provides pharmaceutical preparations for topical use comprising a novel cationic lipid of the invention, having any of the structures disclosed herein together with a pharmacologically effective amount of a therapeutic agent in a pharmaceutically acceptable vehicle. Preferred therapeutic agents are steroids, non-steroidal anti-inflammatory agents, antiviral nucleosides or phospholipid derivatives of these antiviral nucleosides, a therapeutic polynucleotide which is a ribozyme or an antisense RNA or DNA sequence, a polynucleotide coding for a therapeutic protein or polypeptide, or a therapeutic protein or polypeptide itself. The therapeutic protein or polypeptide may be, for example, one that is absent or deficient in a genetic disease, an immunogen, a natural hormone, or a synthetic analogue of a natural hormone.

Included among the particularly preferred embodiments according to this aspect of the invention are topical formulations for the treatment of herpes simplex, comprising a cationic lipid of the invention together with a pharmacologically effective concentration of acyclovir, gancyclovir,1-(2-deoxy-2'-fluoro-1-β-D-arabinofuranosyl)-5-iodocytosine (FIAC) or 1(2'-deoxy-2'-fluoro-1-β-D-arabinofuranosyl)5-iodouracil (FIAU) in an pharmaceutically acceptable vehicle. In preferred embodiments, the preparation comprises phosphoglyceride derivatives of acyclovir, gancyclovir, FIAC or FIAU.

According to another aspect of the invention, there is provided a method for introducing a biologically active agent into a cell, either plant or animal, comprising the steps of preparing lipid vesicles comprising a cationic lipid of the invention, and using these lipid vesicles to facilitate the transfection or transport of bioactive agents into the cells. The intracellular transport may be accomplished by incorporating or encapsulating the bioactive agent in the lipid vesicle and contacting the cell with the lipid vesicles, as in conventional liposome methodology; or alternatively, by contacting the cells simultaneously with empty lipid vesicles, comprising the cationic lipids together with the bioactive agent, according to conventional transfection methodology. In the process of either strategy, the bioactive agent is taken up by the cell. In preferred embodiments of the method, the bioactive agent is a protein, polynucleotide, antiviral nucleoside or a drug. In particularly preferred embodiments, the bioactive agent is an antisense RNA or DNA sequence or a ribozyme. According to one embodiment of the method, the contacting step occurs in vitro. The method may be applied in the treatment of disease in a vertebrate, comprising the step of administering a pharmaceutical preparation comprising any one of the cationic lipids having the structure set forth above together with a pharmacologically effective amount of a therapeutic agent specific for the treatment of the disease to the vertebrate and permitting the therapeutic agent to be incorporated into a cell, whereby the disease is effectively treated. The bioactive agent is delivered to the cells of the animal in vivo or in vitro. The in vitro delivery of a bioactive agent may be carried out on cells that have been removed from an animal. The cells are returned to the animal body whereby the animal is treated.

The methods according to other embodiments of the invention include the topical application of a preparation to the skin; the injection of a preparation into a body cavity or into the tissues of said vertebrate; or the oral administration of said preparation. The biologically active agent can be a polynucleotide, such as, for example, DNA or mRNA coding for a polypeptide, and said polypeptide is expressed after said DNA or said mRNA is taken up into said cell. In yet other embodiments, the biologically active agent is a drug.

The cationic lipids of the invention provide more effective intracellular delivery than the use of presently available agents for the purpose. Further these lipids include species that are less toxic to cells when used in in vivo and in vitro procedures.

These and other advantages and features of the present invention will become more fully apparent from the following description and appended claims.

DETAILED DESCRIPTION OF THE INVENTION

The cationic lipids (CLs) of the invention, comprising compositions having an ammonium group together with hydrophobic alkyl groups, as well as adducts of these cationic lipids, are advantageously used in formulations to prepare lipid vesicles or liposomes to be used in transfection procedures, or to similarly facilitate the intracellular delivery of proteins, polypeptides, small organic molecules, and drugs of therapeutic interest. The adducts further comprise additional cationic and hydrophobic groups that enhance the effectiveness of the lipids in interacting with cell membranes.

We have discovered that certain derivatives and adducts of a compound having the structure

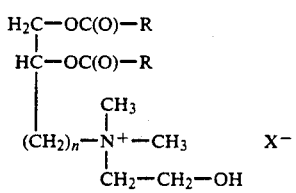

wherein R is a long chain fatty acid, are highly effective compounds for use in lipid formulations for transfection and other intracellular delivery procedures. A single species of a compound of this type, comprising $C_{18}$ (stearoyl) fatty acids was described by Rosenthal, A. F. and R. P. Geyer, *J. Biol. Chem.* 235(8):2202–2206 (1960). The Rosenthal compound, which is an inhibitor of phospholipase A (Rosenthal Inhibitor, RI), is itself ineffective as a promoter of transfection or intracellular delivery. Modifications to the RI molecule that we have discovered to be most effective in conferring transfective properties are substitution of preferred long chain aliphatic groups, selection of preferred acyl (ester) or alkyl (ether) links between the glycerol moiety of RI and the aliphatic groups, and the addition of groups to the hydroxyl moiety which promote interaction with cell membranes. These compounds have proved to be superior in transfective performance to any presently known, including the cationic lipids described in European Application No. 0 187 702 (1986).

Nomenclature

To simplify description, compounds are referred to herein by acronyms, as follows: RI: The Rosenthal Inhibitor

| | |
|---|---|
| RI: | The Rosenthal Inhibitor |
| DORI: | Dioleoyl derivatives of RI having two $C_{18}$ unsaturated (18:1) aliphatic groups, comprising: |
| DORI diester: | DL-1,2-dioleoyl-3-dimethyl-aminopropyl-β-hydroxyethylammonium |
| DORIE diether: | DL-1,2-O-dioleyl-3-dimethylaminopropyl-β-hydroxyethylammonium |
| DORI ester/ether: | DL-1-O-oleyl-2-oleoyl-3-dimethylaminopropyl-β-hydroxyethylammonium |
| OR | |

-continued

| | |
|---|---|
| | DL-1-oleoyl-2-O-oleyl-3-dimethylaminopropyl-β-hydroxyethylammonium |
| DPRI: | Derivatives of RI having $C_{16}$ (16:0) aliphatic groups, comprising: |
| DPRI diester: | DL 1,2-dipalmitoyl-3-dimethylaminopropyl-β-hydroxyethylammonium |
| DPRI diether: | DL 1,2-O-dipalmityl-3-dimethylaminopropyl-β-hydroxyethylammonium |
| DOTMA: | N-[1-(2,3-dioleyloxy)propyl]-N,N,N-trimethyl-ammonium |
| DOTAP: | DL-1,2-dioleoyl-3-propyl-N,N,N-trimethyl-ammonium |
| DPTMA: | DL-(2,3-dipalmityl)-3-propyl-N,N,N-trimethylammonium |

DLYS-DABA-DORI diesters, diethers, or ester/ethers: Lysine-containing adducts of DORI, having lysine groups attached at the hydroxyl group of the β-hydroxyethyl moiety through a diaminobenzoic acid linker, which is optionally joined to DORI through a glycyl spacer.

DLYS-DABA-DPRI diesters, diethers, or ester/ethers: analogues of above DORI compounds, but comprising DPRI.

SPC-DORI diesters, diethers, or ester/ethers: Spermine-containing adducts of DORI, having spermine attached at the hydroxyl group of the β-hydroxyethyl moiety.

SPC-DPRI diesters, diethers, or ester/ethers: analogues of DORI compounds above, but comprising DPRI.

SPC-DABA-DORI diesters, diethers, or ester/ethers: Spermine-containing adducts of DORI, having spermine groups attached at the hydroxyl group of the β-hydroxyethyl moiety through a diaminobenzoic acid linker, which is optionally joined to DORI through a glycyl spacer.

Cationic lipids according to one aspect of the invention have the general formula

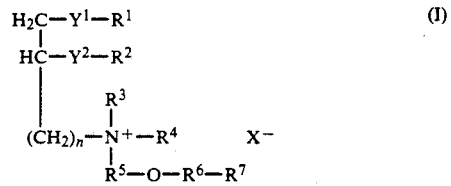

wherein $Y^1$ and $Y^2$ are the same or different and are —O—CH$_2$— —, —O—C(O)—, or —O—;

$R^1$ and $R^2$ are the same or different and are H, or $C_1$ to $C_{23}$ alkyl or alkenyl;

$R^3$ and $R^4$ are the same or different and are $C_1$ to $C_{24}$ alkyl, or H;

$R^5$ is $C_1$ to $C_{24}$ alkyl straight chain or branched chain;

$R^6$ is —C(O)—(CH$_2$)$_m$—NH—, a diaminocarboxylic acid which is alkyl, aryl, or aralkyl, or —C(O)—(CH$_2$)$_m$—NH— linked to said diaminocarboxylic acid, or is absent;

$R^7$ is H, spermine, spermidine, a histone, or a protein with DNA-binding specificity, or wherein the amines of the $R^7$ moiety are quaternized with $R^3$, $R^4$, or $R^5$ groups; or $R^7$ is an L- or D-alpha amino acids having a positively charged group on the side chain, such amino acids comprising arginine, histidine, lysine or ornithine or analogues thereof, or the same amino acids wherein the amine of the $R^7$ moiety is quaternized with $R^3$, $R^4$ or $R^5$ groups; or $R^7$ is a polypeptide selected from the group comprising L- or D-alpha amino acids, wherein at least one of the amino acids residues comprises arginine, histidine, lysine, ornithine, or analogues thereof;

n is 1 to 8;

m is 1 to 18; and

X is a non-toxic anion.

We have determined structure-transfection activity relationships within classes of cationic lipids having a quaternary ammonium group and have found these relationships to be useful in predicting efficient transfection. We accordingly provide synthetic cationic lipids of this class suitable for use in transfection formulations. CLs having long chain aliphatic ($R^1$ and $R^2$) groups comprising ether linkages are preferred to those having ester linkages; CLs having unsaturated $R^1$ and $R^2$ groups are preferred to CLs having corresponding saturated groups; and CLs such as analogues of RI, having polar hydroxyethyl group substituents on the quaternary ammonium group are more effective than those substituted with alkyl groups, for example, the methyl substituent of DOTMA.

Therefore, in particularly preferred embodiments, the cationic lipids of the invention are derivatives of RI having a structure comprising at least one alkyl ether group. A specific memeber of this class of cationic lipids is a DORI diether (DORIE) having long chain alkyl groups with one site of unsaturation, and having the structure:

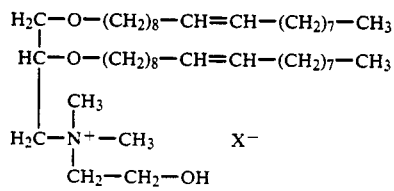

For applications demanding metabolizable, less toxic compounds, CLs having long chain $R^1$ and $R^2$ aliphatic groups attached by acyl bonds are preferred. Therefore, in other preferred embodiments, the cationic lipids of the invention comprise derivatives of RI having the structural characteristics of Formula I, but comprising at least one acyl group, as, for example, a DORI diester having the structure:

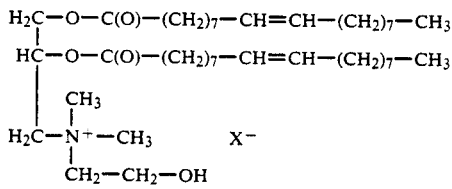

In yet other preferred embodiments, cationic lipids of the invention are substituted at the hydroxyl group of an ethanolamine moiety with various species which act to enhance binding to cell membranes. In preferred embodiments the amine group of ethanolamine is quaternized.

Preferred species for this purpose are compounds such as spermines and spermidines, or other compounds having multiple amino groups, or histones, or similar proteins rich in basic amino acids such as arginine and histidine. Cationic substances such as the histones, spermines, and spermidines are known to bind and modulate negatively charged cell membrane surfaces. For example, lipid-derivatized spermine-like structures are reported to efficiently modulate gene transfer into mammalian endocrine cells (Behr, J.-P. et al. *Proc. Natl. Acad. Sci. USA* 86:6982-6986 (1989). We have designed a series of molecules which combine advantageous properties of both cationic lipids and cationic structures derived from amino acids and spermines. These molecules are prepared by coupling spermine, through a carboxylic acid group, to the hydroxyl moiety of the ethanolamine group of a lipid such as DORI, DORIE or DPRI.

One such series of compounds, is represented by L-spermine-5-carboxyl-3-(DL-1,2-dipalmitoyldimethylaminopropyl-$\beta$-hydroxylamine, designated SPC-DPRI-diester, which has the structure

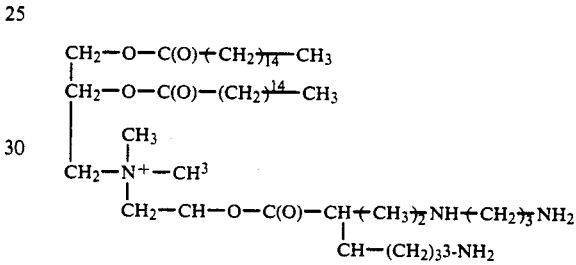

In an example of another lipid of this type, the basic amino acid lysine is linked to the same hydroxyl moiety of the lipid through a linker molecule. The linker molecule can be any diaminocarboxylic acid, either alkyl, aryl or aralkyl, having two amino sites by which lysine is anchored as a pendant in a branched molecule that can bind to multiple binding sites simultaneously. In preferred embodiments, the linker molecule is joined to the hydroxyl group of the hydroxy lipid through a spacer arm which can be any alkyl amino acid. Glycine is a preferred spacer arm. A representative cationic lipid of this type comprises lysine linked to the hydroxyl moiety of DPRI through diaminobenzoic acid and a glycine spacer, to form 3,5-(N,N-di-lysyl)-diaminobenzoyl-glycyl-3-(DL-1,2-dipalmitoyldimethylaminopropyl-$\beta$-hydroxyethylamine). This lipid, designated DLYS-DABA-GLY-DPRI-diester, has the structure

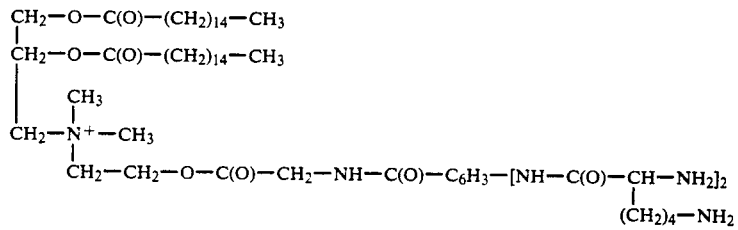

Particularly preferred compounds of this class are DLYS-DABA-GLY-DORI-diester, having the structure

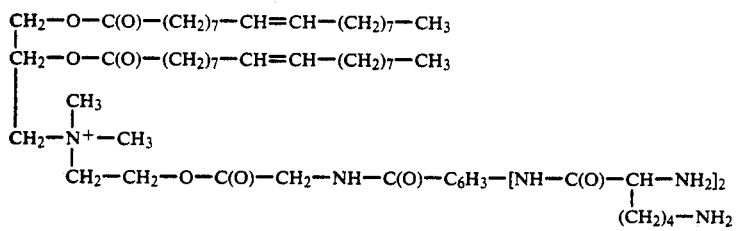

and DLYS-DABA-GLY-DORI-diether, having the structure

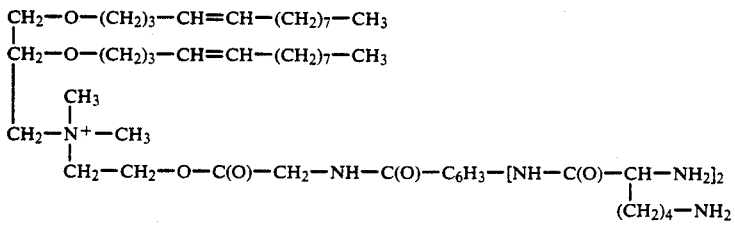

Other molecules of this type can comprise linkers or spacer arms to which are joined other basic amino acids, such as histidine and arginine or analogues or derivatives or these basic amino acids comprising related molecules, which are structurally modified, for example by having substituent groups, such as 1-methyl histidine or 3-methyl histidine. Polymers of these amino acids or their analogues can be attached to the linker in the same manner. Amine-containing groups added to the cationic lipids of the invention through spacers and linkers at the β-hydroxyethylammonium moiety can in turn provide further hydrophobic regions to the lipid structure by quaternization of the amine with the alkyl, alkenyl, aryl and aralkyl groups of $R^3$, $R^4$, and $R^5$. Thus, the assembled lipid adducts, comprising additional cationic groups, and in some cases, additional hydrophobic groups as well, incorporate additional sites capable of interaction with the cell membrane, thereby increasing the intracellular delivery potency of the cationic lipid.

For some applications it is important that cationic lipids used are metabolizable and therefore non-toxic, both for in vitro applications and especially when used in vivo, and yet retain the substantial transfective properties associated with lipid species having an ether-linked alkyl group. Accordingly, we have synthesized cationic lipids according to another aspect of the invention having the formula

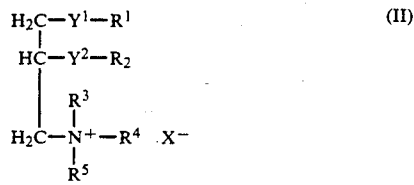

or an optical isomer thereof, wherein $Y^1$ and $Y^2$ are different and are either —O—CH2—, —O—C(O)—, or OH;

$R^1$ and $R^2$ are individually absent or are $C_1$ to $C_{23}$ alkyl or alkenyl;

$R^3$, $R^4$ and $R^5$ are the same or different and are H, $C_1$ to $C_{14}$ alkyl, $C_7$ to $C_{11}$ aryl or aralkyl, or at least two of $R^3$, $R^4$, and $R^5$ are taken together to form quinuclidino, piperidino, pyrrolidino, or morpholino;

n is 1 to 22; and

X is a non-toxic anion.

According to one aspect of the invention, the CLs are combined with other lipids in formulations for the preparation of lipid vesicles or liposomes for use in intracellular delivery systems. The formulations preferably are prepared from a mixture of positively charged lipids, negatively charged lipids, neutral lipids and cholesterol or a similar sterol. The positively charged lipid can be one of the cationic lipids of the invention alone, a mixture of these, or one of the cationic lipids of the invention in combination with the cationic lipids DOTMA, DOTAP, or analogues thereof. Neutral and negatively charged lipids can be any of the natural or synthetic phospholipids or mono—, di-, or triacylglycerols. The natural phospholipids are typically those from animal and plant sources, such as phosphatidylcholine, phosphatidylethanolamine, sphingomyelin, phosphatidylserine, or phosphatidylinositol. Synthetic phospholipids typically are those having identical fatty acid groups, including, but not limited to, dimyristoylphosphatidylcholine, dioleoylphosphatidylcholine, dipalmitoylphosphatidylcholine, distearoylphosphatidylcholine and the corresponding synthetic phosphatidylethanolamines and phosphatidylglycerols. The neutral lipid can be phosphatidylcholine, cardiolipin, phosphatidylethanolamine, mono-, di- or triacylglycerols, or analogues thereof. The negatively charged lipid can be phosphatidylglycerol, phosphatidic acid or a similar phospholipid analog. Other additives such as cholesterol, glycolipids, fatty acids, sphingolipids, prostaglandins, gangliosides, neobee, niosomes, or any other natural or synthetic amphophiles can also be used in liposome formulations, as is conventionally known for the preparation of liposomes.

In a formulation for preparing cationic lipid vesicles, the cationic lipid can be present at a concentration of between about 0.1 mole % and 100 mole %, preferably 5 to 100 mole %, and most preferably between 20 and 100 mole %. The neutral lipid can be present in a concentration of between about 0 and 99.9 mole %, preferably 0 to 95 mole %, and most preferably 0 to 80 mole %. In order to produce lipid vesicles or liposomes having a net positive charge, the quantity of the positively charged component must exceed that of the negatively charged component. The negatively charged lipid can be present at between about 0 to 49 mole % and preferably 0 to 40 mole %. Cholesterol or a similar sterol can be present at 0 to 80 mole %, and preferably 0 to 50 mole %.

Lipid formulations comprising at least one amphipathic lipid can spontaneously assemble to form primary liposomes, heterogeneous in size. Therefore, according to a preferred method, the lipid reagents of the invention, comprising at least one cationic lipid species, are prepared as liposomes according to the procedure of Example 12. The component lipids are dissolved in a solvent such as chloroform and the mixture evaporated to dryness as a film on the inner surface of a glass vessel. On suspension in an aqueous solvent, the amphipathic lipid molecules assemble themselves into primary liposomes. If other molecules are present in the aqueous solvent, such as, for example, a bioactive substance, these will be captured within the liposomes. Otherwise, empty liposomes will be formed. A bioactive substance in the from of its lipid derivative, may be added to the component lipids of the liposome formulation, to be incorporated into the wall of the liposomes on hydration.

These primary liposomes are reduced to a selected mean diameter by means of the freeze-thaw procedure referred to above. The CLs of the invention are formed into vesicles of uniform size prior to transfection procedures, according to methods for vesicle production published in the literature and known to those in the art, for example, the sonication of spontaneously formed liposomes comprised of the lipids in aqueous solution described by Felgner, P. L. et al., *Proc. Natl. Acad. Sci., USA* 84:7413–7417 (1987) or the reverse-phase evaporation procedure of J. Wilschut et al. *Biochemistry* 19:6011–6021(1980) or freeze-thaw and extrusion (Mayer, L. et al., *Biochim. Biophys. Acta* 858:161–168 (1986). To prepare liposomes suitable for physiological in vivo use, having a unilamellar structure and a uniform size of from about 50 to about 200 μm in diameter, the primary liposomes are preferably processed by the freeze-thaw and extrusion processes.

Other suitable conventional methods of preparation include, but are not limited to, those disclosed by Bangham, A. et al., *J. Mol. Biol.* 23: 238-252 (1965); Olson, F. et al., *Biochim. Biophys. Acta* 557: 9–23 (1979), Szoka F. et al., *Proc. Natl. Acad. Sci. USA* 75: 4194–4198 (1978), Mayhew, E. et al. *Biochim. Biophys. Acta* 775: 169–175 (1984), Kim, S. et al. *Biochim. Biophys. Acta* 728:339–348), and Fukunaga, M. et al. *Endocrinol.* 115:757–761 (1984).

Transfection Parameters

We have discovered that several factors affect the efficiency of cationic lipid-mediated transfection as determined by the level of gene product produced. 1. Cationic Lipid Formulations Lyso Lipid Compounds Incorporation of a quantity of a single chain phosphatide into the lipid formulation for transfection has the effect of increasing the efficiency of transfection.

As demonstrated in Example 20, the addition of monooleoyl lysophosphatidylcholine to a transfection formulation comprising DOTMA and DOPE (Lipofectin ™), in amounts up to a molar ratio of lysophosphatide to DOTMA of 0.5, can increase the efficiency of transfecting DNA coding for β-galactosidase into cells by an amount greater than 100%.

According to current theories of self-assembling lipid structures, the combined thermodynamic forces of packing constraints and the interactive free energies of lipid polar headgroups with an aqueous media determine the geometry and structure of lipid vesicles. Entropy favors small structures, and packing constraints oppose close packing. Accordingly, in an aqueous media, the entropically favored structures for homogenous systems of single-chain lipids are single layer micelle structures having a relatively small radius of about 15-20 Angstrom units, while those for corresponding systems of double-chain lipids, whose lipid chains cannot be so tightly packed, are double layered structures having aqueous interiors with wall thicknesses of about 50 Angstroms (Israelachvili, J. N. et al.; *Biochim. Biophys. Acta* 470:185–201 (1977).

At high concentrations of lipids, vesicles interact with one another to aggregate, fusing together the outer lipid membranes of each. Membrane fusion is a phenomenon that occurs broadly in biological processes. It is this phenomenon which causes lipid vesicles to fuse with the lipid bilayer of cell membranes whereby the contents of the lipid vesicle are delivered into the cell cytoplasm. However, when the fusogenic properties of lipid vesicles causes their aggregation with each other, their diameter can increase to beyond that of the effective range for transfection. Fusogenic behavior of cationic lipid vesicles resulting in aggregation of the vesicles is induced by the presence of anions in the aqueous media which interact with the cationic polar headgroups of the lipid formulations (Duzgunes, N. et al., *Biochemistry* 29:9179-9184 (1989).

It is believed that the presence of effective concentrations of single chain lipids in the lipid formulation opposes fusogenic behavior leading to aggregation, while preserving the fusogenic behavior that allows vesicle contents to be delivered into cells. Single chain lipids can shift the thermodynamic equilibria of lipid systems to allow closer packing and to favor the stability of formed lipid vesicles so as to resist aggregation. As levels of single-chain lipids increase, however, the efficiency of transfection no longer is improved, but declines. This effect may be due to an increase in the resistance of the lipid vesicles to fusion which inhibits fusion with cell membranes or to toxic properties of the single-chain (lyso) lipids, or to both effects.

Accordingly, improved transfection formulations contain amphipathic lipids comprising a polar headgroup and having a single lipid chain in amounts capable of promoting transfection while preserving the ability of the lipid vesicles assembled from the formulation to achieve fusion with cell membranes.

Suitable lyso lipids comprise lysophosphatides of phospholipids having a neutral, positively charged, or negatively charged headgroup. Phospholipids having a neutral headgroup are preferred. Particularly preferred lysophosphatide species are lysophosphatidylcholine and lysophosphatidylethanolamine. Other suitable single chain lyso lipids comprise any of the cationic lipid compounds of formula I or formula II wherein either $Y^1$ and $R^1$ together or $Y^2$ and $R^2$ together are —OH. Preferred cationic lipids for this purpose comprise Rosenthal Inhibitor ester and ether derivatives disclosed herein as well as lyso forms of DOTMA, DOTAP, and similar saturated analogues, and containing typically $C_{14}$, $C_{16}$, and $C_{18}$ alkyl chains.

The single chain lyso lipid compounds have been found to be effective in molar ratio concentrations of up to 0.5 relative to the concentration of the double lipid chain cationic lipids of the transfection formulations.

Presence of a Neutral Lipid

Figure 3:
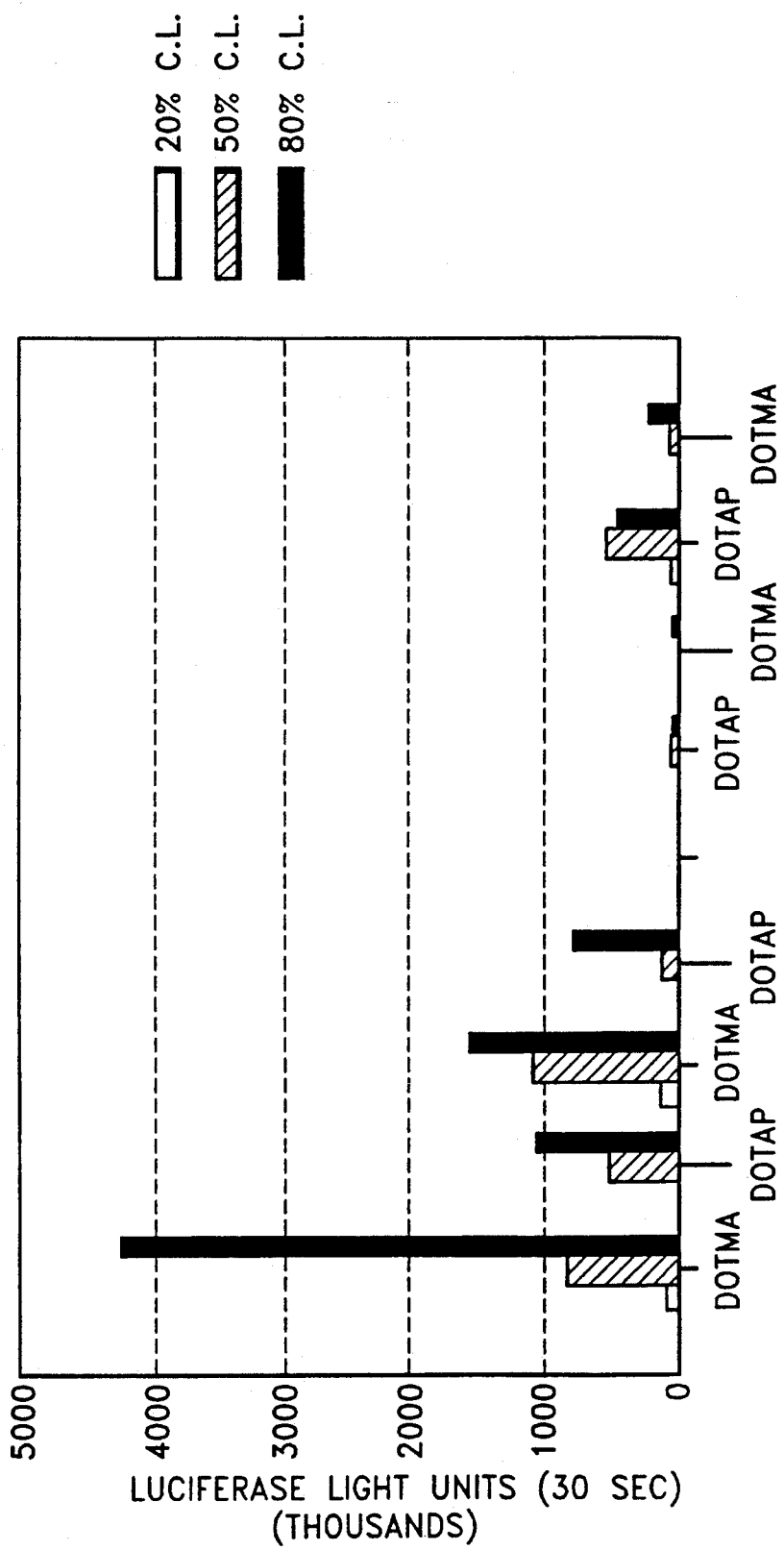
FIG. 3 demonstrates the effect of cationic lipid concentration on the effectiveness of RNA transfection using DOTAP and DOTMA as cationic lipids.
Figure 4:
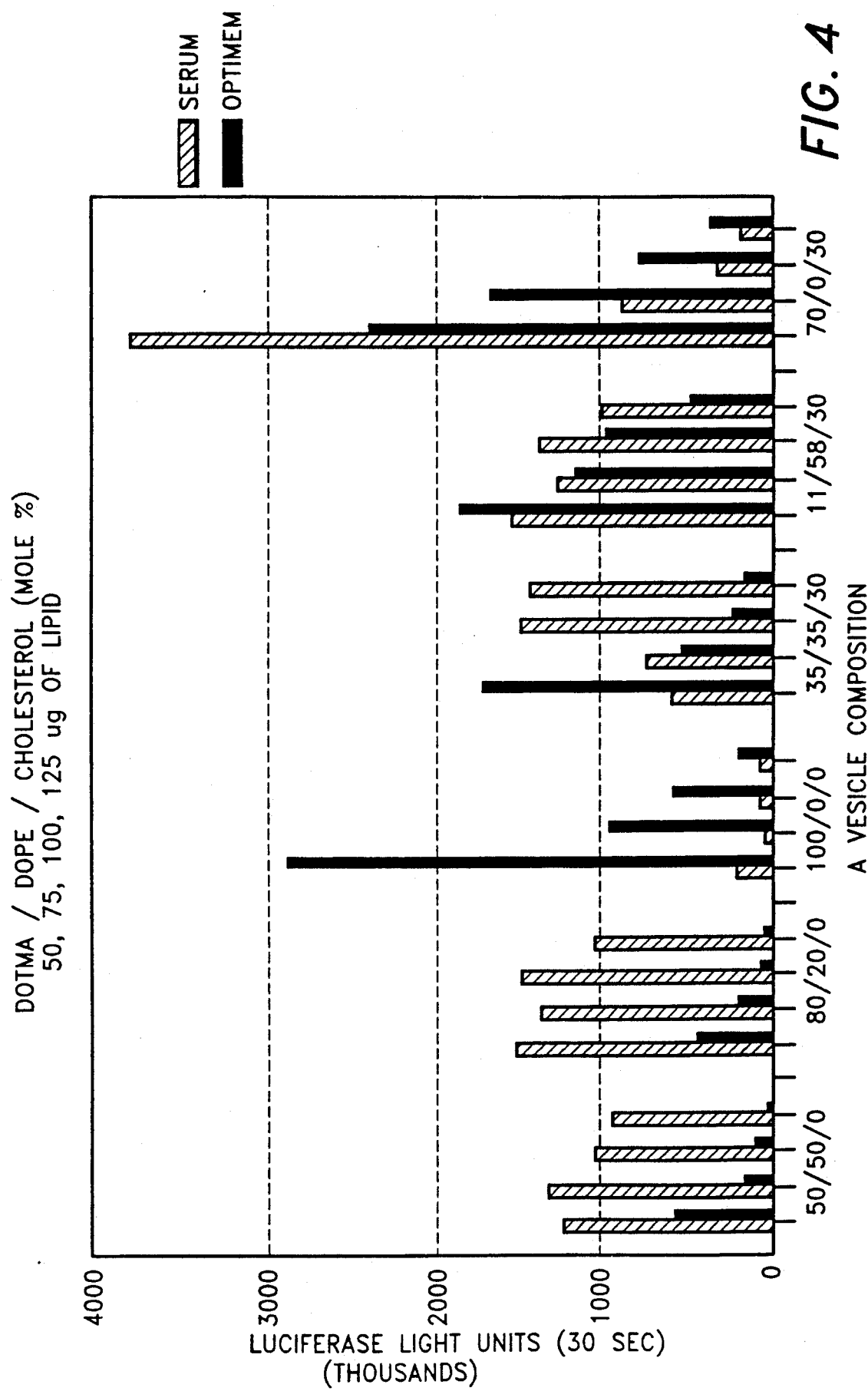
FIG. 4 demonstrates the effect of neutral lipids on the comparative effectiveness of a series cationic lipids in promoting RNA transfection.
Figure 6A:
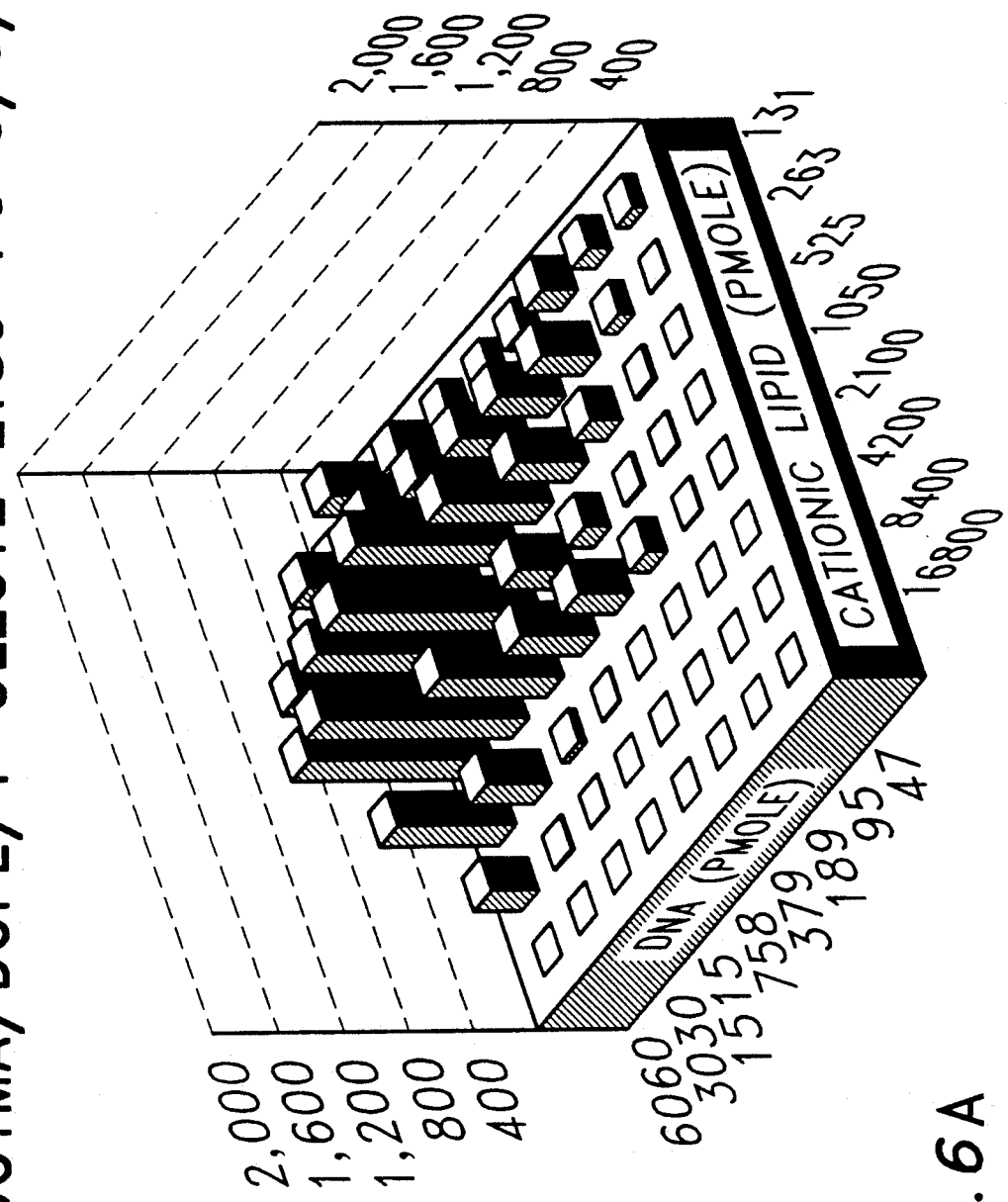
FIGS. 6a–6d demonstrate the effect of increasing relative concentrations of lysophosphatidylcholine in lipid formulations on DNA transfection efficiency as demonstrated by expression of gene product in cell culture.
Figure 6B:
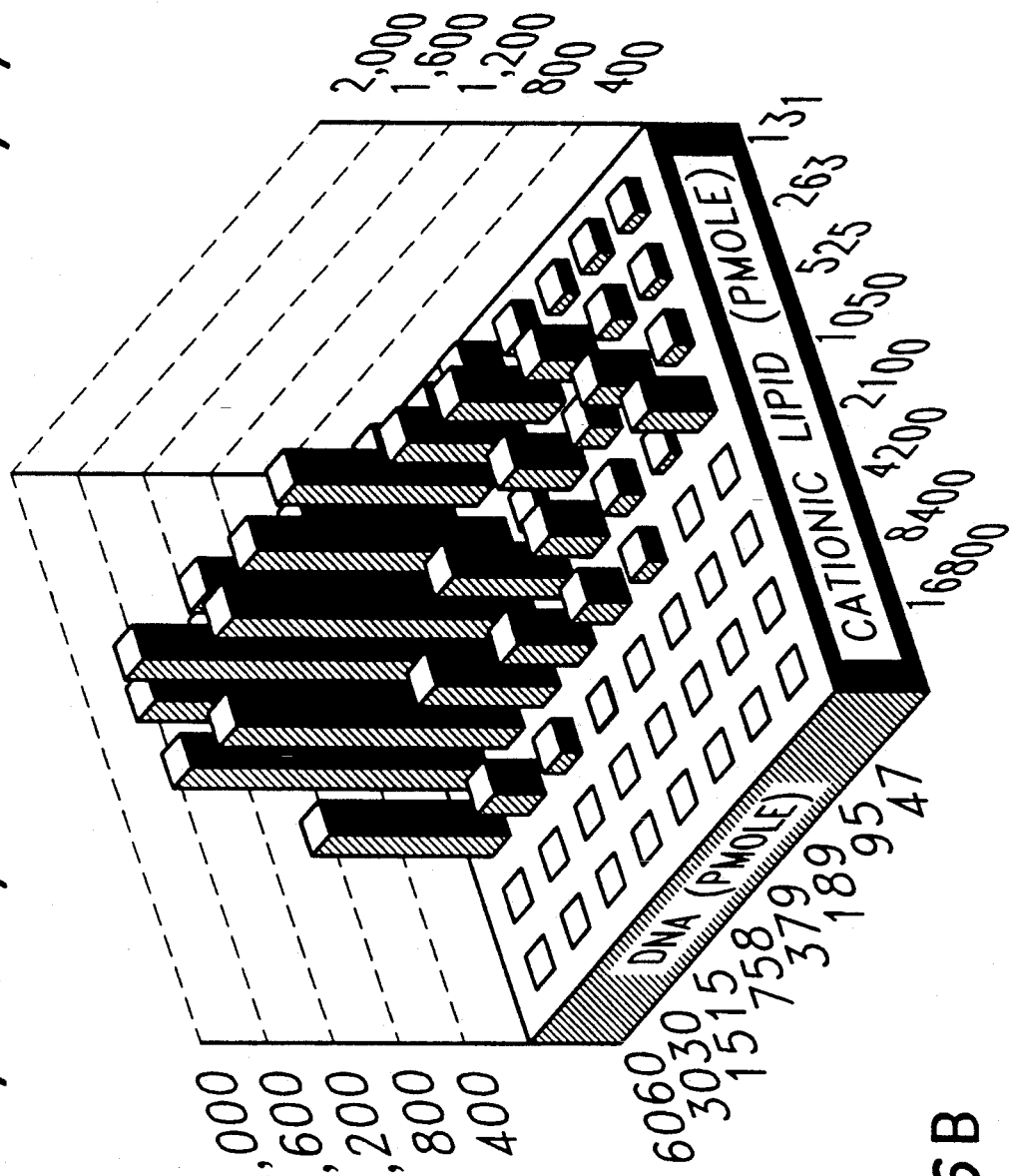
Figure 6C:
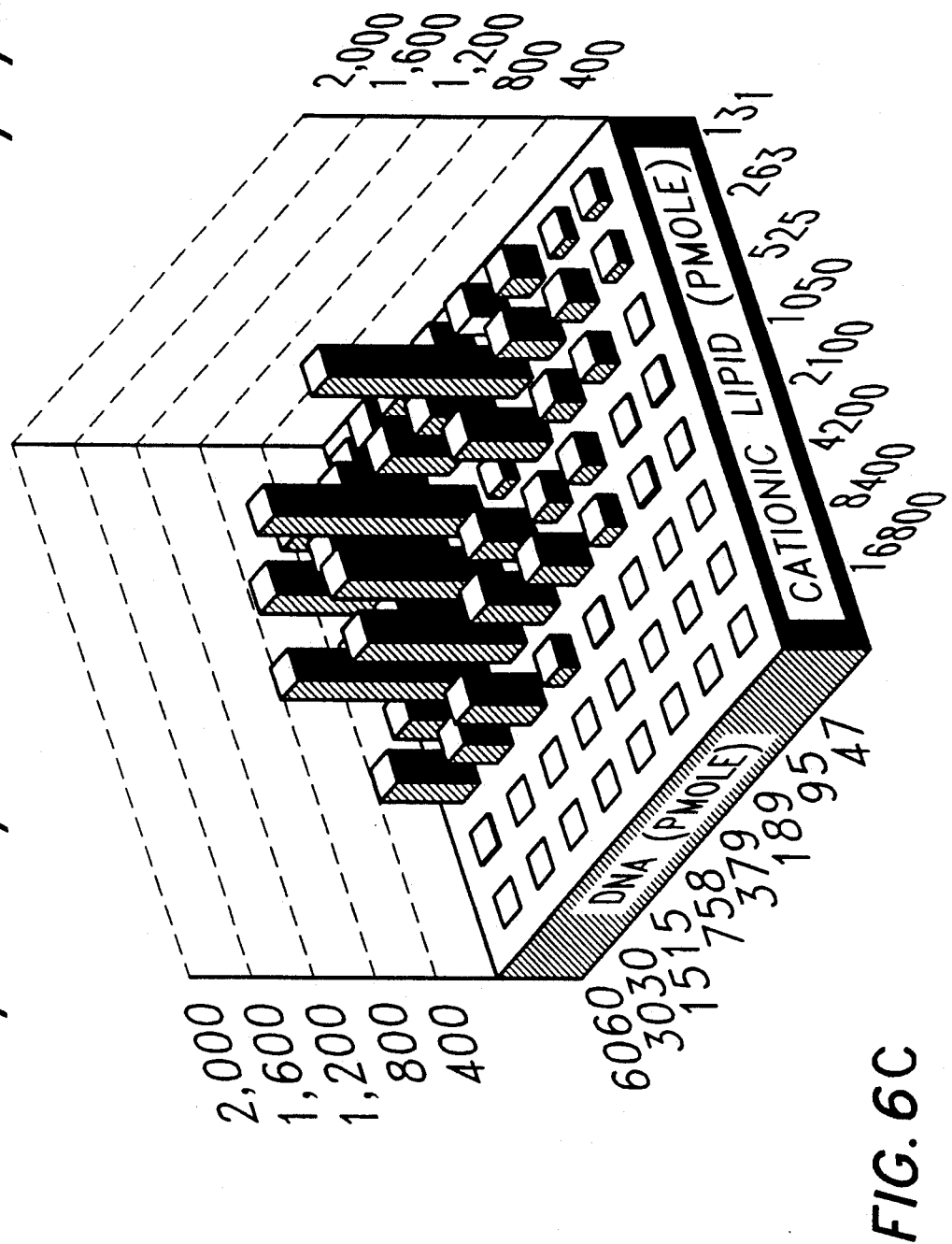
Figure 6D:
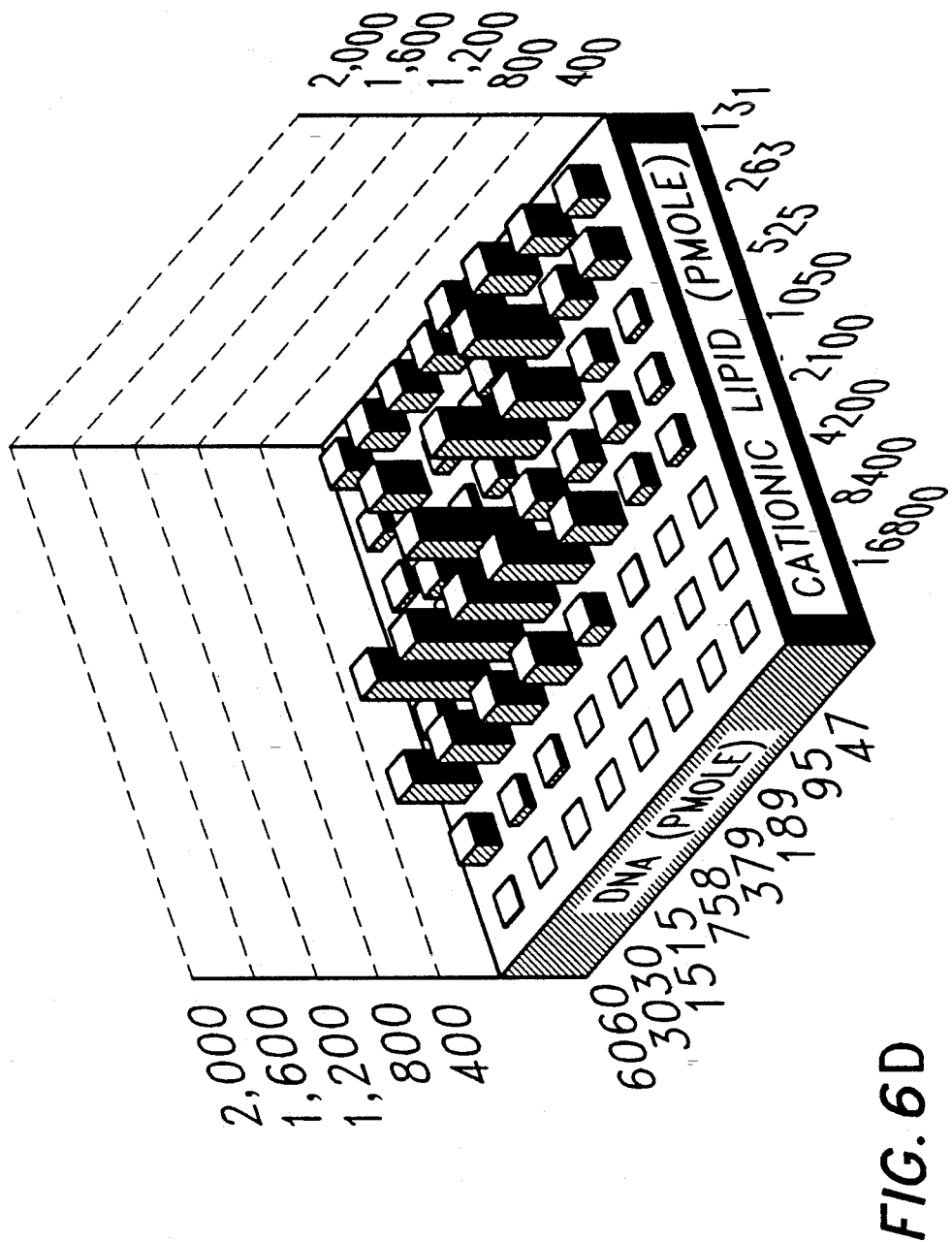
Figure 7A:
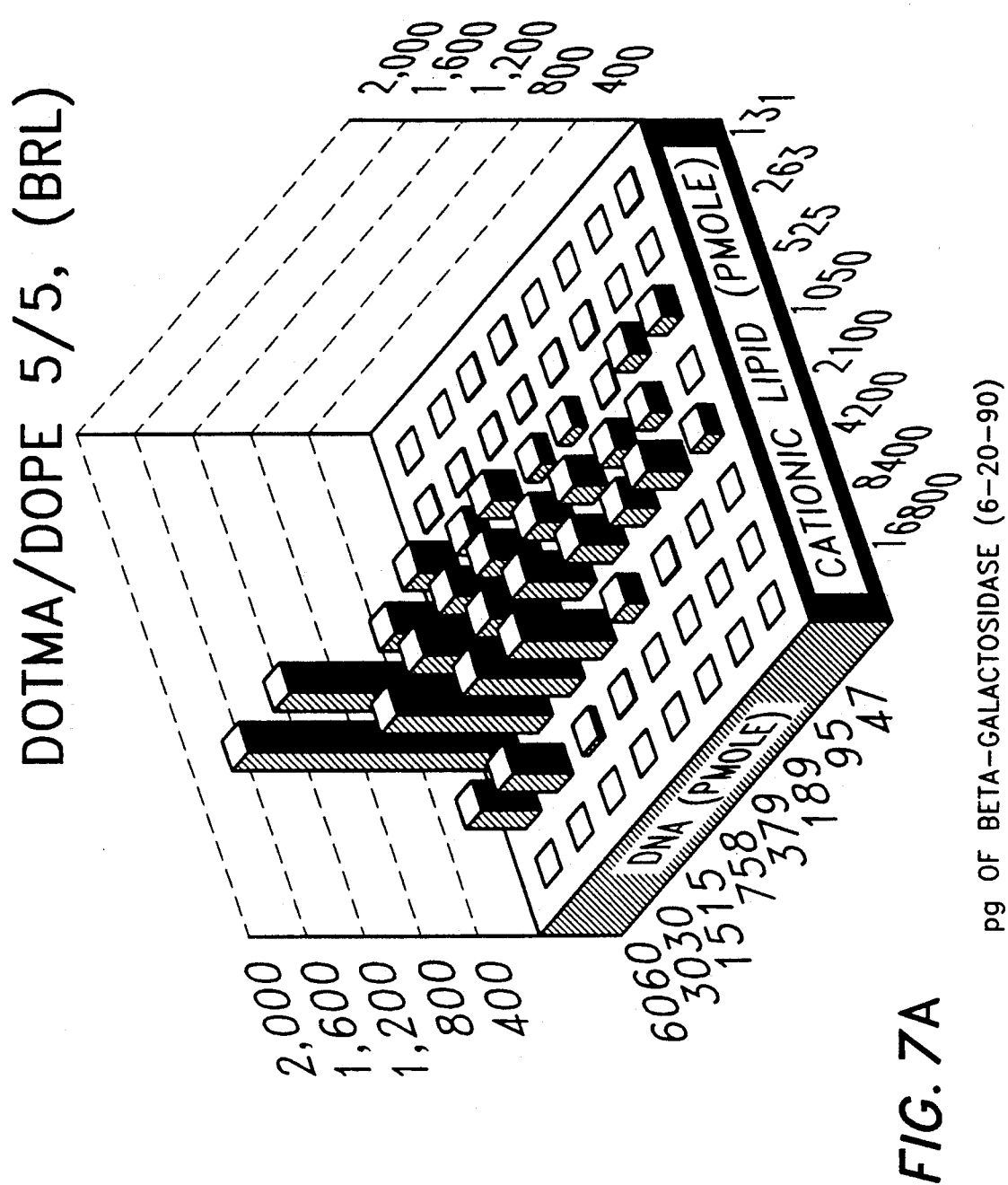
FIGS. 7a–7c demonstrate the comparative DNA transfection activity of various cationic lipid analogs.
Figure 7B:
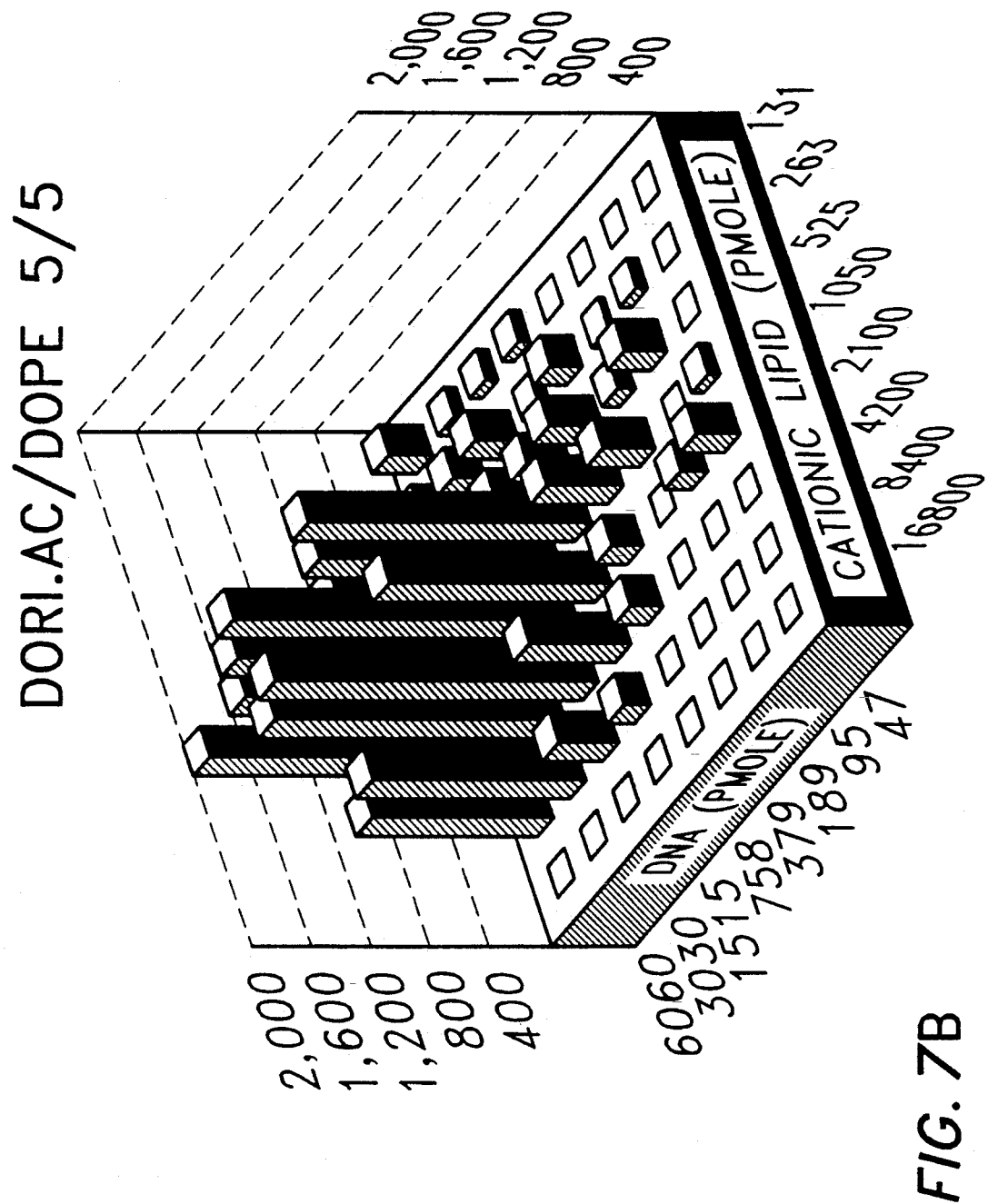
Figure 7C:
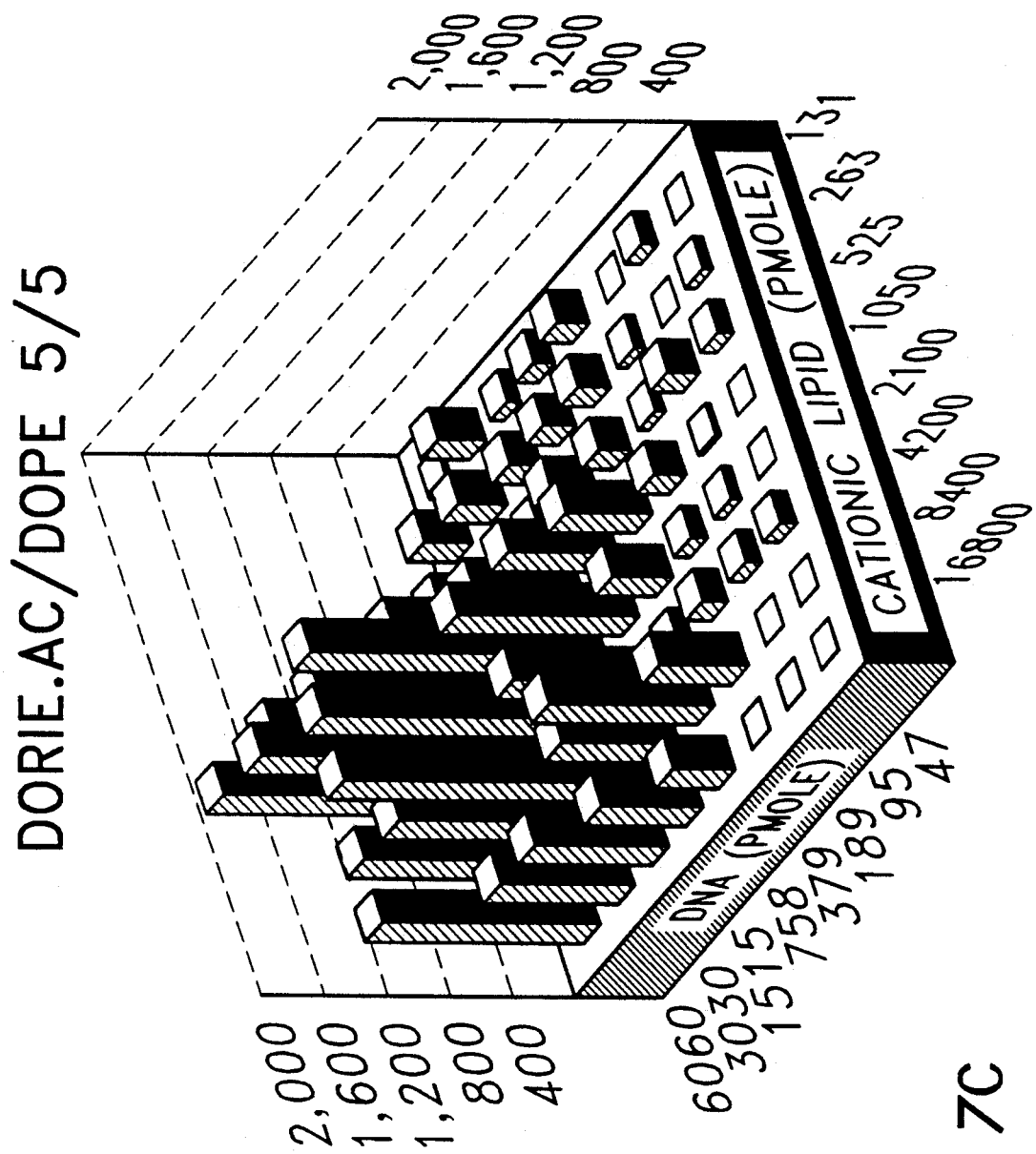
Figure 8A:
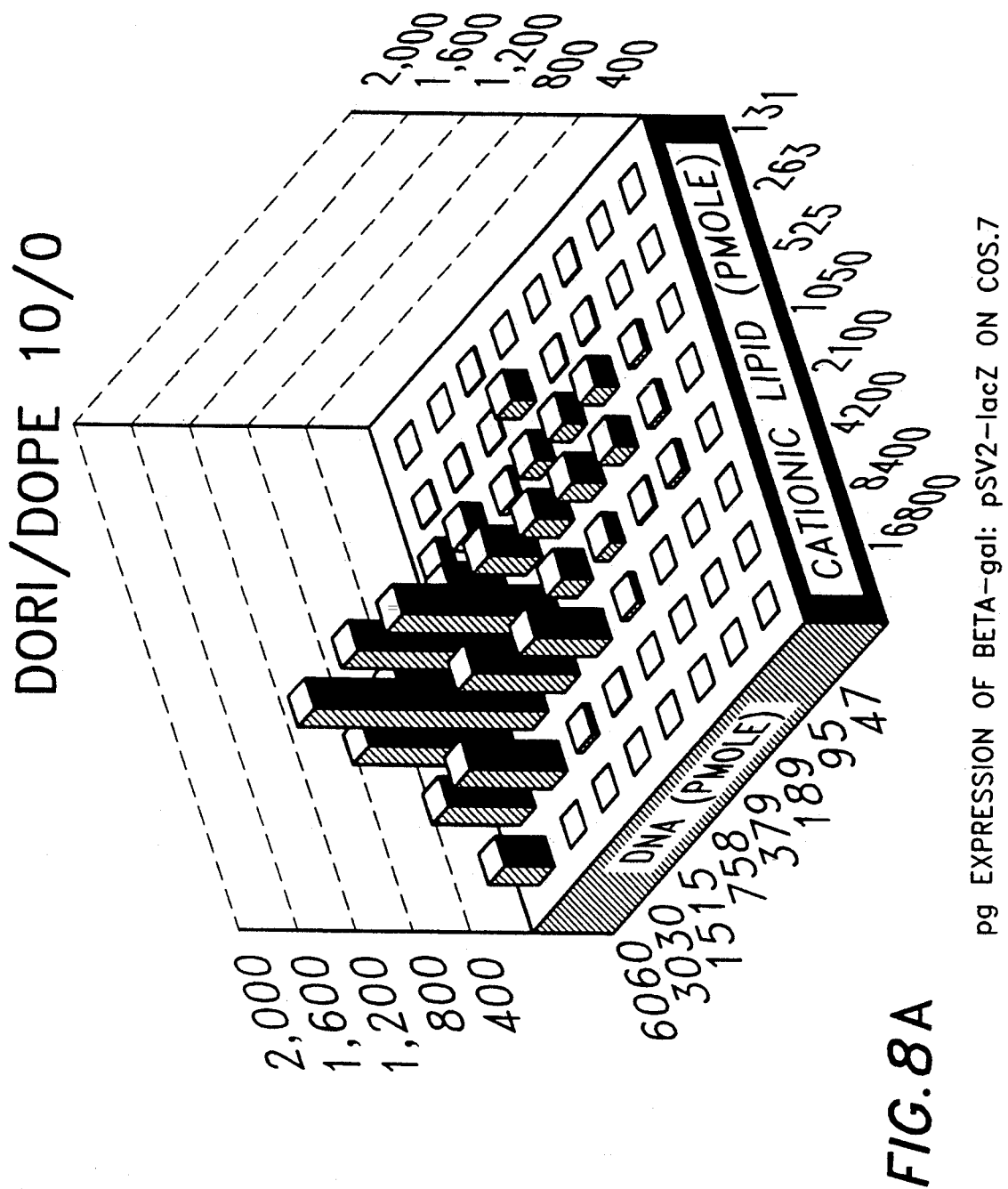
FIGS. 8a–8d demonstrate the effect of neutral phospholipids in the transfection lipid formulation on the efficiency of DNA transfection.
Figure 8B:
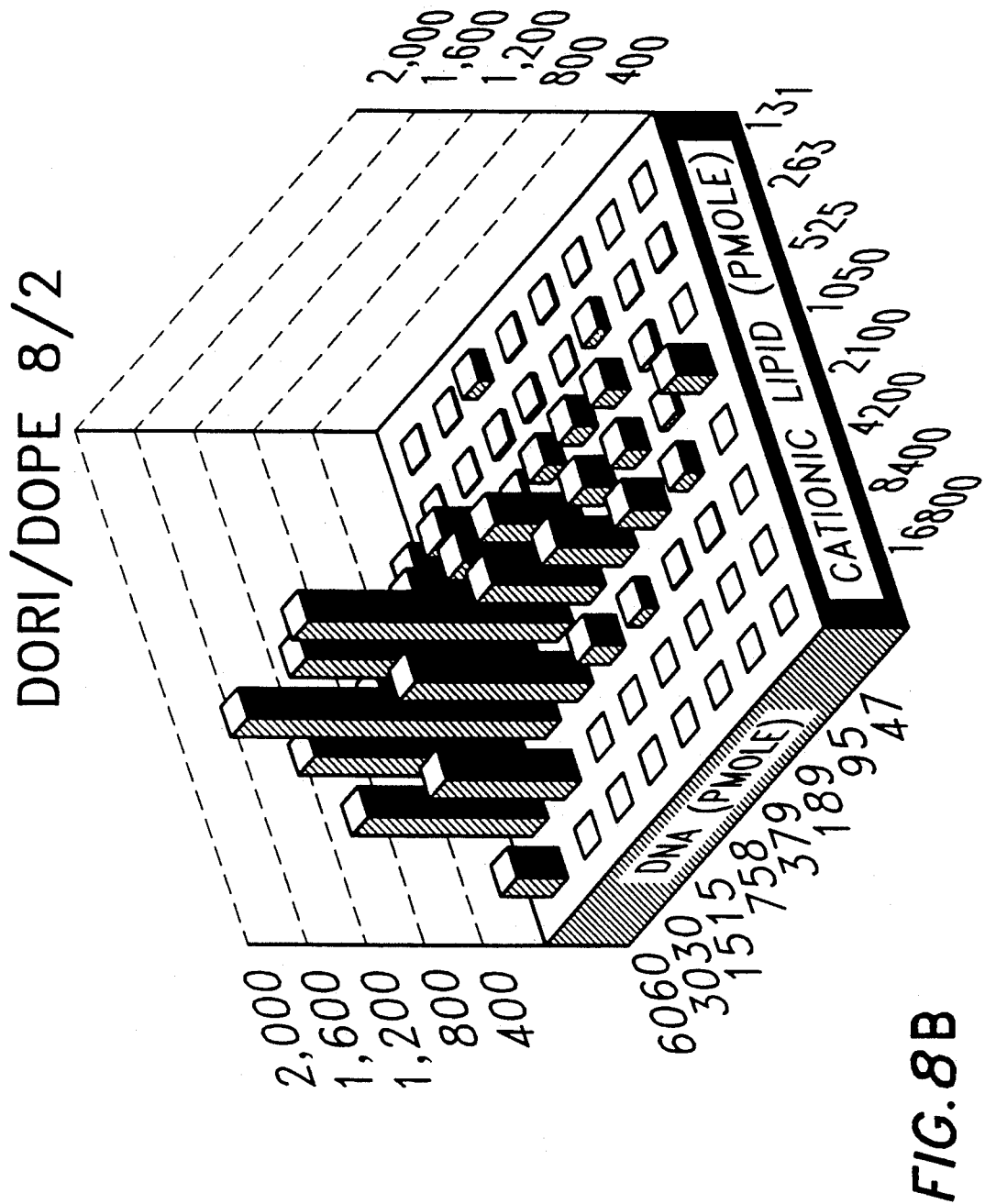
Figure 8C:
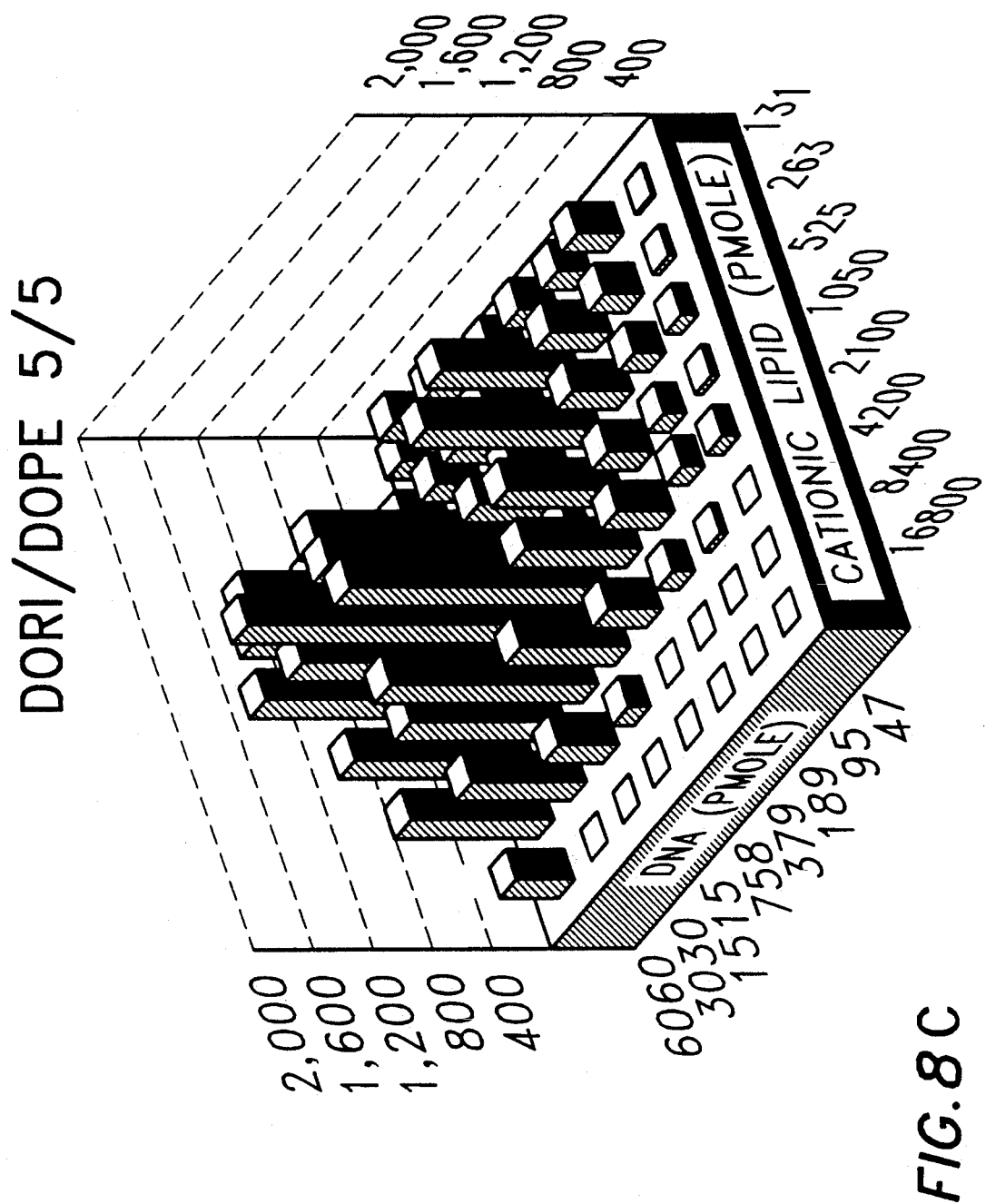
Figure 8D:
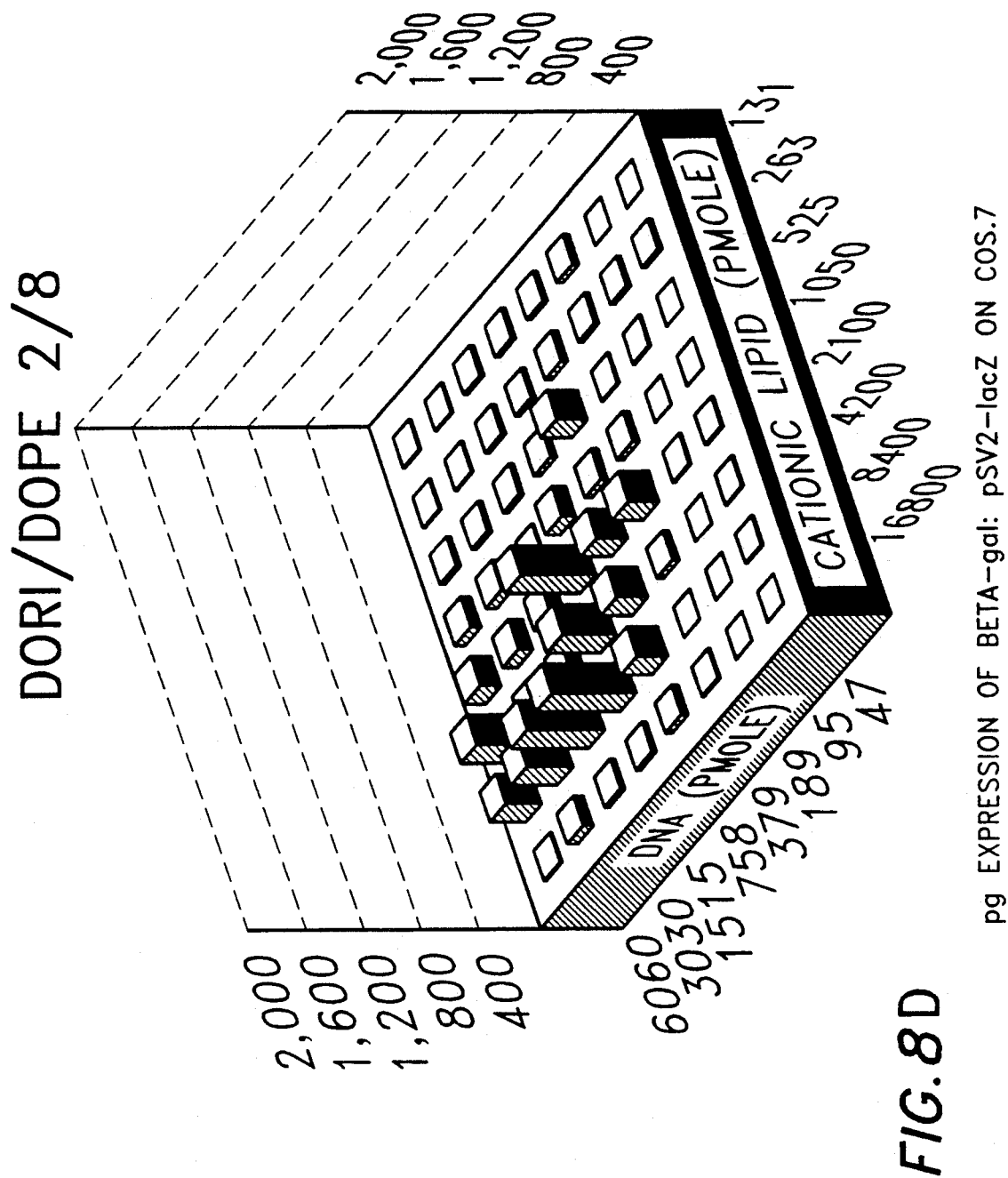

Under some conditions, the presence of a neutral lipid in the transfection lipid formulation appears to reduce the efficiency of transfection. The presence of DOPE or DOPC reduced the effectiveness of DOTMA in RNA transfection, while cholesterol was less inhibitory (Examples 17 and 18; FIGS. 3-4). However, DORI was most effective in DNA transfection when combined with DOPE in a molar ratio of 5/5 (Example 22; FIG. 8). The effect may be related to the physical structure of the transfected polynucleotide. 2. Transfection Conditions

Presence of Serum

Although the presence of serum appears to inhibit the formation of cationic lipid/RNA complexes, the presence of serum in the transfection procedure itself, that is, after the addition of cationic lipid/polynucleotide complexes formed in the absence of serum, is only slightly inhibitory (Examples 15 and 22). Previous results seem to indicate that serum inhibits transfection; however, these experiments (FIGS. 1-5) shows comparatively good activity even in the presence of serum.

Cell Density

Cationic lipid-mediated transfections can be effectively carried out over a range of cell densities. Transfection of pSV2-lacZ into COS.7 cells was carried out according to the procedure of Example 14B at cell densities from 5,000 cells/well to highly confluent cells at 40,000 cells/well. The successful transfection of highly confluent cells indicates that cell division is not required for either expression or functional delivery of DNA; however, optimal expression was observed at 20,000 cells/well (90% confluency). Further decreasing cell density to 5,000 to 10,000 cells/well led to a shift of optimal expression to lower lipid concentration. This result may be due to higher toxicity (greater amount of cationic lipid per cell) and in general a lower expression corresponding to the lower number of cells.

Choice of Cell Line for Transfection

Transfection of pSV2-lacZ using a DORI/DOPE 5/5 lipid formulation under the protocol of Example 14B was carried out for a number of different cell lines. A wide range of β-galactosidase activity, from 50 pg/well to 20,000 pg/well was determined among these cells, as follows:

| | |
|---|---|
| L-M | 50 pg |
| L-929 | 80 pg |
| CV-1 (ATCC CCL70) | 900 pg |
| COS.7 (ATCC CRL 1651) | 1000-2000 pg |
| BHK (ATCC) | 20,000 pg |

The enormous variation in the level of expression is probably caused by differences in both DNA uptake as well as intracellular metabolic factors. It is a factor to consider when the yield of gene product is a priority.

Applications

The cationic lipids of the invention can be advantageously used, either alone or in combination with other known cationic lipids such as for example, DOTMA or DOTAP, in any procedure comprising the use of liposomes or lipid vesicles to deliver substances intracellularly either in vitro or in vivo. Those lipids having metabolizable ester bonds are preferred for in vivo use.

1. Production of Gene Product

Contemplated uses comprise transfection procedures corresponding to those presently known and using amphipathic lipids, including commercial cationic lipid preparations, such as Lipofectin TM, and using conventional cationic lipid technology and methods. Accordingly, the lipid compositions disclosed herein can be used to facilitate the intercellular delivery of DNA or mRNA sequences coding for therapeutically active polypeptides, as described in detail in U.S. patent applications Ser. Nos. 326,305 and 467,881 which are hereby incorporated by reference. They can be similarly used for the liposomal delivery of the expressed gene product, the polypeptide or protein itself. Thus cationic lipid mediated delivery of DNA and mRNA polynucleotides or proteins can provide therapy for genetic disease by supplying deficient or absent gene products to treat any genetic disease in which the defective gene or its product has been identified, such as Duchenne's dystrophy (Kunkel, L. and Hoffman, E. *Brit. Med. Bull.* 45(3):630-643 (1989) or cystic fibrosis (Goodfellow, P. *Nature,* 341(6238):102-3 (Sep. 14, 1989).

The cationic lipid-mediated intracellular delivery described above can also provide immunizing polypeptides to the cell, either by delivering a polynucleotide coding for the immunogen, or the immunogen itself.

The transfection procedures described above may be applied by direct injection of cationic lipids together with DNA, RNA or proteins into cells of an animal in vivo. However, it has been recently shown that cationic lipids are particularly effective at facilitating in vitro transfection of cells. Therefore the above therapies can be alternatively carried out by in vitro transfection of some of the cells of an animal using cationic lipid delivery methods, and reintroduction of the cells into the animal. The ability to transfect cells at high efficiency with cationic lipids thus provides an alternate method for immunization. The gene for an antigen is introduced, by means of cationic lipid-mediated delivery, into cells which have been removed from an animal. The transfected cells, now expressing the antigen, are reinjected into the animal where the immune system can now respond to the (now) endogenous antigen. The process can be enhanced by co-injection of either an adjuvant or lymphokines, or a gene coding for such lymphokines, to further stimulate the lymphoid cells.

Cationic lipid methodology is preferred over other methods; it is more convenient and efficient than calcium phosphate, DEAE dextran or electroporation methods.

Other therapeutically important polynucleotides suitable for cationic lipid mediated delivery are negatively charged novel oligonucleotides of various technologies, including antisense polynucleotide sequences, useful in eliminating or reducing the production of a gene product, as described by Ts'o, P. et al. *Annals New York Acad. Sci.* 570:220-241 (1987). Many of these oligonucleotide species, which are scarce and expensive to synthesize, are inefficiently captured by encapsulation into liposomes of negatively charged lipids, according to ordinary current methods. We have experimental studies showing that these oligonucleotides are captured within cationic liposomes with efficiencies approaching 100%. Also within the scope of the invention is the delivery, by means of the cationic lipids disclosed, of ribozymes, or catalytic RNA species, either of the "hairpin" type as described by Hampel et al. *Nucleic Acids Research* 18(2):299–304 (1990); or the "hammerhead" type described by Cech, T. and Bass, B. *Annual Rev. Biochem.* 55:599–629 (1986).

Particularly preferred contemplated uses of the invention are deliveries of either an antisense polynucleotide or ribozyme as described above, and having as its target the rev site of the HIV genome (*Scientific American*, October, 1988, pp. 56–57). Matsukura, M. et al. *Proc. Nat'l. Acad. Sci.* 86:4244–4248 (1989) describe a 28-mer phosphorothioate compound anti-HIV (anti-rev transactivator) specific for the site.

Other therapeutic uses of cationic lipids herein disclosed include the liposomal delivery of nucleoside or nucleotide analogues having an antiviral effect, such as dideoxynucleotides, didehydronucleotides, nucleoside or nucleotide analogues having halo-substituted purine or pyrimidine rings such as 5-trifluoromethyl-2'-deoxyuridine or 5-flurouracil; nucleoside or nucleotide analogues having halo- and azido-substituted ribose moieties, such as 3'-azido-3'deoxythymidine (AZT), nucleoside analogues having carbon substituted for oxygen in the ribose moiety (carbocyclic nucleosides), or nucleotide analogues having an acyclic pentose such as acyclovir or gancyclovir (DHPG). The liposomal delivery of such analogues is disclosed in U.S. patent application Ser. No. 099,755 filed September, 1987 by Hostetler and Richman. The antiviral potency of these analogues is found to be increased when they are presented to the cells as phospholipid derivatives. These derivatives may be incorporated into the liposomal structure for administration to cells thereby forming a more stable liposomal complex which can deliver greater amounts of drugs to target cells with less toxicity. Effective antiviral lipid derivatives of nucleoside analogues comprise phosphatidyl 2',3'-dideoxynucleosides, 2',3'-didehydronucleosides, 3'-azido-2'-deoxynucleosides, 3'-fluorodeoxynucleosides and 3'-fluorodideoxynucleosides, 9-β-D-arabinofuranosyladenine (araA), 1-β-D-arabinofuranosylcytidine (araC), nucleosides such as acyclovir and gancyclovir having an acyclic ribose group, or the same nucleoside analogues as diphosphate diglyceride derivatives. Preferred species of lipid derivatives of antiviral or antiretroviral nucleoside analogues for the treatment of HIV infection using cationic lipid mediated liposomal delivery are phospholipid derivatives of 3'-azido-2', 3'-dideoxypyrimidine, 3'-halopyrimidine dideoxynucleoside, or a 2',3'-didehydro-2',3'-dideoxynucleoside, for example, phosphatidyl 3'-azido-3'deoxythmidine (pAZT) or phosphatidyl 2-chlorodeoxyadenosine. Certain viral infections, comprising herpes, cytomegalovirus, and hepatitis B infections are effectively treated with nucleoside analogues comprising acyclovir, gancyclovir, 1-(2-deoxy-2'-fluoro-1-β-D-arabinofuranosyl)-5-iodocytosine (FIAC) or 1(2'-deoxy-2'-fluoro-1-β-D-arabinofuranosyl)5-iodouracil (FIAU). Phospholipid derivatives of these agents, preferably the phosphatidyl and diphosphate diglyceride derivatives can be administered in these diseases using cationic lipid liposomal delivery systems, according to the invention. Details of the structures, synthesis and liposomal delivery of lipid derivatives of antiviral nucleosides are presented in U.S. patent applications Ser. Nos. 216,412; 319,485; and 373,088 which are hereby incorporated by reference.

Among other therapeutically important agents that can be thus delivered are peptides comprising physiologic species such as interleukin-2, tumor necrosis factor, tissue plasminogen activator, factor VIII, erythropoietin, growth factors such as epidermal growth factor, growth hormone releasing factor, neural growth factor, and hormones such as tissue insulin, calcitonin, and human growth hormone as well as toxic peptides such as ricin, diphtheria toxin, or cobra venom factor, capable of eliminating diseased or malignant cells.

Use of the disclosed lipids is also contemplated for the encapsulation of various other agents to be delivered intracellularly according to methods known to those skilled in the art, and as described in Duzgunes, N., *Subcellular Biochemistry* 11:195–286 (1985). Materials to be delivered can be proteins or polypeptides, especially negatively charged molecules, monoclonal antibodies, RNA-stabilizing factors and other transcription and translation regulating factors, antisense oligonucleotides, ribozymes, and any molecule possessing intracellular activity. Such encapsulation further protects the described agents from non-productive sequestration by substances of the extracellular environment.

Pharmaceutical Formulations

The cationic lipids of the invention can be used in pharmaceutical formulations to deliver therapeutic agents by various routes and to various sites in the animal body to achieve a desired therapeutic effect. Local or systemic delivery of the therapeutic agent can be achieved by administration comprising application or insertion of the formulation into body cavities, inhalation or insufflation of an aerosol, or by parenteral introduction, comprising intramuscular, intravenous, intradermal, peritoneal, subcutaneous and topical administration. The effect of the cationic lipids in these formulations is to enhance the potency and efficiency of the therapeutic agent contained therein by facilitating its intracellular delivery.

Topical formulations are those advantageously applied to the skin or mucosa. Target mucosa can be that of the gastrointestinal tract, comprising the mouth, naso-pharynx and stomach, or the vaginal or anorectal mucosa. Other target tissues can be the accessible surfaces and canal of the ear and the ocular tissues. Cationic lipids present in topical formulations can act to facilitate introduction of bioactive molecules into the target tissue, such as the stratum corneum of the skin, by perturbing the barrier properties of the protective membrane, or by introducing perturbing agents or penetration enhancers such as Azone TM or by promoting the activity of these penetration enhancers.

Several classes of drugs consisting of small organic molecules can be delivered in the formulations as described above. One such class comprises steroidal anti-inflammatory agents which may be prepared in liposomal formulations for topical application. Drugs of this class comprise hydrocortisone, fluocinolone acetonide, available as Synalar TM (Syntex, Palo Alto, Calif. 94303); fluocinonide, available as Lidex TM (Syntex, Palo Alto, Calif. 94303); and dexamethasone, available as Decaderm TM (Merck, Sharpe and Dohme, West Point, Pa. 19486).

Other topical formulations comprising the cationic lipids are preparations comprising topical antibiotics such as clindamycin, tobramycin, neomycin, gentamycin, tetracycline, erythromycin; oxidants such as benzoyl peroxide; antifungal agents, such as clotrimazole, miconazole, nystatin, lactoconazole, econazole, and tolnaftate; retinoic acid for the treatment of acne; and agents for the treatment of herpes simplex and comprising antiviral nucleoside analogues such as acyclovir and gancyclovir. These nucleoside analogue formulations preferably comprise lipid derivatives of the antiviral agents, particularly the phosphatidylglycerol derivatives as disclosed in U.S. application Ser. No. 373,088, and as such may be incorporated into liposomes comprising one or more cationic lipids of the invention.

Other pharmaceutical formulations comprising the cationic lipids of the invention are topical preparations containing an anesthetic or cytostatic agent, immunomodulators, bioactive peptides or oligonucleotides, sunscreens or cosmetics. Preparations for topical use are conveniently prepared with hydrophilic and hydrophobic bases in the form of creams, lotions, ointments or gels; alternatively, the preparation may be in the form of a liquid that is sprayed on the skin. The effect of the cationic lipids is to facilitate the penetration of the active antiviral agent through the stratum corneum of the dermis.

Similar preparations for opthalmic use are those in which the pharmacologically effective agent is timolol, betaxolol, levobunalol, pilocarpine, and the antibiotics and corticosteroids disclosed for topical applications.

Another group of drugs can be delivered orally, topically, or systemically with the cationic lipid materials according to formulations of the invention are nonsteroidal anti-inflammatory agents, such as, for example, 1-acetylsalicylic acid (aspirin; Bayer); piroxicam, available as Feldene ® (Pfizere, New York, N.Y. 10017); (Z)-5-fluoro-2-methyl-1-[[p-alcohol(methylsulfinyl)-phenyl]methylene]1-H-indene-3-acetic acid (sulindac), available as Clinoril TM (Merck, Sharpe and Dohme, West Point, Pa. 19486); 2-[(2,6-dichlorophenyl)amino]-benzeneacetic acid, monosodium salt (diclofenac), available as Voltaren TM (Ciba-Geigy, Summit, N.J.): 2',4'-difluoro-4-hydroxy-3-biphenylcarboxylic acid (diflunisal), available as Dolobid TM, (Merck, Sharpe and Dohme); 1-(4-chlorobenzoyl)-5-methoxy-2-methyl-1H-indole-3-acetic acid (indomethacin), available as Indocin TM (Merck, Sharpe and Dohme); (±)-2-(p-isobutylphenyl)propionic acid (ibuprofen), available as Advil TM (Whitehall laboratories, Inc., New York, N.Y. 10017); N-(2), 6-dichloro-m-tolyl) anthranilic acid (meclophenomate), available as Meclomen TM (Parke-Davis, Morris Plains, N.J. 07950; fenoprofen, an arylacetic acid derivative, available as Nalfon TM (Dista Products Co., Indianapolis, Ind. 46285; 2-naphthaleneacetic acid, 6-methoxy-alpha-methyl-, (±) (naproxyn), available as Naprosyn TM (Syntex, Palo Alto, Calif. 94303); 1-methyl-5-(4-methyl-benzoyl)-1H-pyrrole-2-acetate dihydrate (tolmetin), available as Tolectin TM (McNeil Pharmaceutical, Spring House, Pa. 19477); and derivatives and congeners thereof.

The composition and form of pharmaceutical preparations comprising the cationic lipids disclosed, in combination with a drug or other therapeutic agent, can vary according to the intended route of administration.

Orally administered preparations may be in the form of solids, liquids, emulsions, suspensions, or gels, or preferably in dosage unit form, for example as tablets or capsules. Tablets may be compounded in combination with other ingredients customarily used, such as talc, vegetable oils, polyols, gums, gelatin, starch, and other carriers. The lipid vesicles may be dispersed in or combined with a suitable liquid carrier in solutions, suspensions, or emulsions.

Parenteral compositions intended for injection, either subcutaneously, intramuscularly, or intravenously, can be prepared either as liquids or solid forms for solution in liquid prior to injection, or as emulsions. Such preparations are sterile, and liquids to be injected intravenously should be isotonic. Suitable excipients are, for example, water, dextrose, saline, and glycerol.

The cationic lipids of the invention may also be present in liquids, emulsions, or suspensions for delivery of active therapeutic agents in aerosol form to cavities of the body such as the nose, throat, or bronchial passages. The ratio of active ingredient to the cationic lipid and the other compounding agents in these preparations will vary as the dosage form requires.

Preparation of Cationic Lipid Compounds

A. Derivatives of the Rosenthal Inhibitor

Cationic lipids of the invention which are analogues of the Rosenthal inhibitor may be synthesized by acyl and alkyl substitution of a 3-dimethylaminopropane diol, followed by quaternization of the amino group as described in Examples 1 through 5. Alkyl substitution of the primary and secondary alcohol groups of the diol to from a diether derivative is accomplished by treating the 3-dimethylamino-1,2-propanediol with an alkyl or alkenyl methanesulfonate in a neutral solvent, such as benzene, as described in Example 1 for the synthesis of 1,2-0-dioleoyl-3-dimethylamino propyl-$\beta$-hydroxyethylammonium acetate. Acyl substitution of the primary and secondary alcohol groups to form a diester derivative is accomplished by treating 3-dimethylaminopropanediol with an acyl halide in a suitable solvent at an elevated temperature for an extended time, as described in Example 3 for the synthesis of DL-1,2-dioleoyl-3-dimethylaminopropyl-$\beta$-hydroxyethylammonium acetate. The synthesis of mixed acyl/alkyl derivatives is accomplished by blocking the primary or secondary alcohol groups of the starting diol, for example by benzylation, to form a lyso compound, which, on condensation with an alkyl or alkenyl methanesulfonate, yields a 1-O-benzyl-, 2-O-alkyl glycerol derivative. Debenzylation, followed by acylation with an acyl halide yields a 1-acyl, 2-O-alkyl derivative. Alternatively, the diol can be alkylated with an alkyl methanesulfonate, and the 1-alkyl, 2-lyso derivative isolated and acylated with an acyl anhydride as described in Example 6, part A.

Quaternization of the thus-substituted diol is carried out by treatment with a quaternizing group in the form of a halo derivative, and in the presence of a basic catalyst, such as 4-dimethylaminopyridine.

B. Synthesis of Rosenthal Inhibitor adducts comprising additional cationic and hydrophobic moieties One type of cationic lipid composition having multiple amino groups present is prepared by attaching a molecule which is basic in nature and of the type known to bind to DNA, such as for example a histone, spermine or spermidine through a carboxyl group attached to the basic molecule (J.-P. Behr et al., *Proc. Natl. Acad. Sci. USA* 86:6982–6986 (1989)) to the available hydroxyl group of a DORI or DPRI diester, diether, or ester/ether using a condensing reagent, as for example, dicyclohexylcarbodiimide (DCC).

Another approach, comprising the attachment of pendant lysine groups, uses a linker molecule capable of bonding to the available hydroxyl group of an hydroxylipid and having at least two sites capable of bonding to lysine. This approach is exemplified by attaching two lysine groups to DPRI-diester through diamino benzoic acid.

C. Synthesis of ester/ether derivatives of DOTMA, DOTAP and their analogues

Cationic lipids corresponding to Formula II and having both an acyl and alkyl group attached thereto are synthesized essentially as described in U.S. Pat. No. 4,897,355, which is hereby incorporated by reference, except that 3-(dialkylamino)-1,2-propane diols (designated Formula 3 therein) are converted to mixed acyl/ether derivatives according to the procedure of Example 6.

Any of the cationic lipid molecules of the invention can be synthesized to contain alkyl chains which are linked to the glycerol moiety by either ester linkages or by ether linkages. Accordingly, the molecules may be either diester, diether, 1-ether-2-ester or 1-ester-2-ether. The structure-transfection activity relationships indicate that for optimal polynucleotide delivery the molecules should be of the diether type; however, these molecules are difficult to metabolize in vivo and would be expected to result in toxic effects due to accumulation of the lipids in the body. The diester compounds should be readily metabolized; however, these compounds are less active at delivering polynucleotide than the corresponding diether cationic lipids. The etherester molecules will have transfection activity that is intermediate between diether and diester molecules, but unlike the diether molecules, ether-ester molecules can be metabolized and excreted by the body. Analogous phospholipids, for example the platelet aggregating factor, 1-O-alkyl-2-acetyl-sn-glycero-3-phosphopholine, are metabolized by several cell types, including epithelial cells of the lung and skin fibroblasts (Kumar, R. et al. *Biochim. Biophys. Acta* 917:33–41 (1987). This feature of the ester/ether species of cationic lipids is significant in view of studies indicating liposome mediated transfection can occur with significant efficiency in vivo, for example in infusion into the trachea (Brigham, K. L. et al. *Amer. J. of the Medical Sciences* 298(4):278–281 (1989). Due to improved transfection activity and metabolizability of ether/ester molecules, these agents will have particular advantages both in vitro and in vivo.

Non-toxic salts of the compounds described herein are included within the scope of the invention. Such salts may be prepared from pharmaceutically non-toxic acids including inorganic acids and organic acids. Such acids include hydrochloric, hydrobromic, sulfuric, phosphoric, acetic, benzoic, citric, glutamic, lactic acid and the like. For the preparation of pharmaceutically acceptable salts, see S. M. Berge et al., *Journal of Pharmaceutical Sciences*, 66:1-19(1977) which is incorporated herein by reference. Cationic lipid reagents of the invention may be prepared and stored in aqueous solution as empty liposomes, or may be stored dry after formulation to be later used as encapsulating agents for selected bioactive substances.

Optimal Transfection and Intracellular Delivery Parameters

Accurate evaluation of the effectiveness of cationic lipid species in achieving intracellular delivery requires that structure-activity relationships be determined using an optimized standard formulation and procedure.

We have investigated the optimal conditions using DOTMA, a cationic lipid known to be an effective transfection agent, according to the experiments as follows.

A. Characteristics of the Media

The critical procedural issue in cationic lipid mediated transfection relates to how serum is introduced into the transfection procedure. The studies of Examples 15 and 16 show that the presence of serum in a first step, wherein the lipid vesicles form complexes with polynucleotide molecules, is inhibitory to transfection. However, when the complexes are first allowed to form in the absence of serum, these complexes can be added into tissue culture media containing low concentrations (5 to 15%) of serum without such inhibition. Note that in FIG. 2 a dramatic increase in the functional delivery and expression of mRNA occurs in comparison to FIG. 1.

Figure 2:
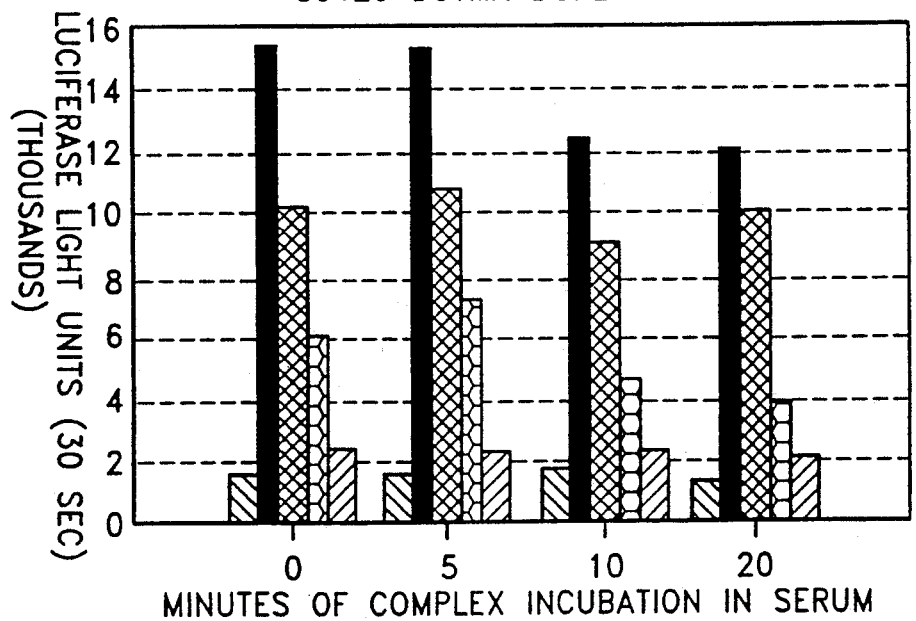
FIG. 2 demonstrates the effect of serum on the effectiveness of RNA transfection.

Moreover, cells transfected by the methodology represented in FIG. 2 not only express the gene product more efficiently, but they also look visibly healthier under the microscope. Toxicity studies using trypan blue exclusion indicate that cells can withstand higher cationic lipid concentration in the presence of serum.

B. Characteristics of the Lipid Formulation

The critical formulation features for optimal activity were identified by comparing the effectiveness of 24 cationic lipid formulations in transfecting cells with messenger RNA containing a luciferase message. FIG. 3 shows results from transfections using Lipofectin TM (DOTMA:DOPE 50:50) showing cationic lipid doseresponse and serum effects. Higher lipid concentrations are required for the maximum response in the presence of serum.

Since formulations containing increasing quantities of a neutral lipid appear to be increasingly less active, some alternative formulations, lacking the neutral phospholipid component, were tested. Transfection formulations were prepared both with and without a neutral phospholipid component according to the procedures of Examples 7, 8 and 9. The cationic lipid DOTMA was combined in formulations either alone or combined with cholesterol and compared with similar formulations comprising the neutral lipid DOPE as indicated in the table of Example 18 below. The highest activity occurs in formulations lacking the phospholipid component, particularly in the presence of cholesterol. FIG. 4 taken from the same set of transfections, indicates that the newly defined cationic lipid composition (DOTMA/DOPE/Cholesterol 70/0/30), containing no phospholipid, gives rise to much higher levels of mRNA expression (compare the scales on the y-axis of the two FIGS. 3 and 4) and that this reagent has similar activity in the presence and absence of serum.

Comparison of More Polar Specie's of Corresponding Cationic Lipids

The transfection effectiveness of a group of cationic lipids was evaluated under optimal transfection conditions determined as described; that is using lipid formulations in the ratio CL/cholesterol of 70/30 with no phospholipid component, and allowing the first stage association of lipid vesicles and mRNA to occur in the absence of serum. As in the previous examples, tissue culture 3T3 mouse cells were transfected with RNA coding for the luciferase enzyme. The commercially available Rosenthal Inhibitor (RI), DL-2,3-distearoyloxypropyl(dimethyl)-$\beta$-hydroxyethylammonium bromide (Sigma, St. Louis, Mo.), was prepared as lipid vesicles according to Example 11 and was found to have very weak activity as a cationic lipid for use in transfections. The DPRI diester (dipalmitoyl), and DORI diester (dioleoyl) derivatives of RI were synthesized. We also synthesized (2,3-dipalmitoyl)-prop-1-yl-N,N,N-trimethylammonium (DPTMA)), an analogue of DOTMA, a cationic lipid known to be an effective agent. The synthesized lipids as well as DOTMA itself, N-[1-(2,3-dioleyloxy)propyl]-N,N,N-trimethylammonium were evaluated for their ability to transfect the tissue culture cells with luciferase RNA. Data are presented in FIG. 5. The primary finding is that the hydroxyethyl moiety present at the hydrophilic site in the Rosenthal inhibitor increases the transfective effectiveness of cationic lipids as compared to corresponding cationic lipids lacking this group. Further, the representative cationic lipid of the invention, DORI, is a more effective transfective agent than DOTMA, even though it lacks the ether groups shown in previous examples, to confer superior transfective activity. It should be noted that DOTMA, under the optimized transfective conditions of these experiments, has greatly enhanced transfective properties as compared to commercial Lipofectin ™. Further, the superior transfective agent DORI is superior as a metabolizable, non-toxic transfective agent.

In summary, these studies indicate that effective transfection of cells using CLs requires selecting the most effective cationic lipid for the application, the optimal transfection formulation, and the use of an optimal transfection procedure.

The invention can be better understood by way of the following examples which are representative of the preferred embodiments thereof, but which are not to be construed as limiting the scope of the invention.

EXAMPLE 1: Synthesis of 1,2-0-dioleyl-3-dimethylamino propyl-$\beta$-hydroxyethylammonium acetate (DORI diether)

Step (a): Oleylmethanesulfonate

In a 500 ml three-necked flask equipped with a dropping funnel, 5.0 g (18.7 mmoles) of oleyl alcohol (Nu Check Prep, Elysian, Minn. 56028) was dissolved in 6.67 ml of dry pyridine and 100 ml of freshly distilled chloroform. The solution was chilled in an ice bath and 3.22 g (28.14 mmoles) of methanesulfonyl chloride (Nu Check Prep) dissolved in 50 ml of dry chloroform was added dropwise during one hour. The reaction mixture was allowed to stir for another 4 hours at room temperature. At the end of the reaction period, 30 ml of ice cold water and 50 ml of diethylether was added. The organic layer was washed twice with 50 ml of 0.5N cold HCL, followed by 50 ml of cold 0.5N sodium bicarbonate. Finally, the organic phase was dried over anhydrous sodium sulfate and evaporated under vacuum on a rotary evaporator. The product was dissolved in 45 ml of absolute ethanol and crystallized at −20° C. Pure long needles of oleylmethanesulfonate were obtained in 90% yield.

Step (b): 1,2-O-dioleyl-3-dimethylaminopropylglycerol

Racemic 3-(dimethylamino)-1,2 propanediol (Aldrich Chemical, Milwaukee, Wis.), 1.5 g, 8.3 mmoles, and potassium hydroxide, 3.7 g in 100 ml of freshly distilled dry benzene was refluxed for 2 hours in a 300 ml, three-necked, round bottom flask fitted with a Soxhlet apparatus containing molecular sieves. Oleyl methanesulfonate, 5.78 g, dissolved in 100 ml of dry benzene, was dropped slowly into the reaction mixture and refluxing was continued for another 4 hours. At the end of the reaction period, cold water and diethylether were added. The organic phase was washed with acid and bicarbonate successively as described above. The crude yellow product gave three spots on thin layer chromatography on silica gel G plates, developed with chloroform/acetone/methanol/acetic acid/water, (50/15/5/5/2) by volume. The required compound was purified by silicic acid column chromatography as follows: Approximately 3.0 g of the above material was loaded on the silica CC 7, BioRad (40.0 g) column and sequentially eluted with chloroform (200 ml), chloroform/methanol 5%, (200 ml), 10% (250 ml) and finally with methanol (500 ml). The pure compound was eluted with 10% methanol fractions and gave an Rf value of 0.45 when chromatographed on the silica gel G plates developed in the above system.

Step (c): 1,2-0-dioleyl-3-dimethylamino propyl-$\beta$-hydroxyethylammonium acetate Racemic 1,2-0-dioleyl-3-dimethylaminopropylglycerol, 2.1 g, (3.4 mmol) and 4 ml of 2-bromoethanol (Aldrich Chemical, Milwaukee, Wis.) in 18 ml of dimethylformamide was added in a 100 ml round bottom flask and stirred for 36h at 45° C. At the end of the reaction period, the mixture was concentrated under reduced pressure, and the product was purified by passing through the silica gel column. The compound was dissolved in a small amount of chloroform and loaded on to 30 gms of silica gel 60, 70–270 mesh, packed in a 1 × 18 column. The pure compound was eluted with 8% methanol in chloroform and gave an Rf value of 0.21 on silica gel G plates developed in the above system. Finally, the bromide salt was converted to acetate by passing the product through a Whatman DE-52 cellulose (acetate form) column. The product was obtained in 50/50 chloroform/methanol eluate. The compound was crystallized in acetonitrile at −20° C.

EXAMPLE 2: Synthesis of DL 1,2-0-dipalmityl-3-dimethylamino propyl-$\beta$-hydroxyethylammonium acetate (DPRI diether)

This compound was synthesized by substituting palmityl alcohol for oleyl alcohol in the above procedure.

EXAMPLE 3: Synthesis of DL-1,2-dioleoyl-3-dimethylaminopropyl-$\beta$-hydroxyethylammonium acetate (DORI diester)

To 10 g. of oleoyl chloride in 21 ml of dry dimethylformamide were added 1.6 g of Rac-3-(dimethylamino)-1,2 propanediol and 5 ml of tributyl. The mixture was heated to 60°–65° C. for 48 hours. After the mixture was cooled to room temperature, 50 ml of freshly distilled diisopropylether was added and the mixture was heated to boiling. The reaction mixture was again cooled to room temperature and filtered. Filtrate was evaporated under vacuum and the product was crystallized with acetonitrile. The pure dioleoyl-3-dimethylaminopropyl-glycerol was further subjected to quaternization by treatment with 2-bromoethanol in dimethylformamide as described in Example 1 above.

EXAMPLE 4: Synthesis of DL-1,2-dipalmitoyl-3-dimethylaminopropyl-β-hydroxyethylammonium (DPRI diester)

This compound was synthesized by using palmitoyl chloride instead of oleoyl chloride in the above procedure.

EXAMPLE 5: Synthesis of DL-1,2-dioleoyl-3-propyltrimethylammonium chloride (DOTAP).

To 2.0 g of 3-(dimethylamino)-1,2-propanediol, dissolved in 15 ml of freshly distilled chloroform and 10 ml of anhydrous pyridine, chilled to 4° C., was added dropwise 12.6 g of oleoylchloride, dissolved in 50 ml of chloroform, over a period of one hour. The reaction was allowed to stir overnight and then stopped by the addition of 50 ml of cold water and ether. The organic phase was washed twice with 0.5N HCL and 0.5N sodium bicarbonate, and after drying over anhydrous sodium sulfate, evaporated under vacuum. The product was purified by silicic acid column chromatography as described in Example 1. The pure compound was next quaternized with methyl chloride as follows: 500 mg of the pure compound was added into the protein hydrolysis tube and the methyl chloride (Aldrich Chemical, Milwaukee, Wis.) was condensed into the tube by repeated cooling of the tube in liquid nitrogen until filled with 5 ml of methyl chloride. The tube was once again thawed, frozen and evacuated with oil pump to remove any residual air. Finally, the tube was sealed and placed in the heated metal block maintained at 70° C. for 72 hours. After the reaction period, the tube was cooled to 0° C. and then opened to evaporate unreacted methyl chloride. The yellow wax was crystallized from acetonitrile at −20° C. Further purification of the compound was done on the silica gel 60 column. The pure compound was eluted with 200 ml of 10% methanol in chloroform and gave an Rf value of 0.23 on a silica gel G plates, when developed in the above solvent system.

EXAMPLE 6: Synthesis of DL 1,2-dipalmitoyl-3-propyltrimethylammonium chloride (DPTMA diester).

This compound was synthesized by using palmitoyl chloride instead of oleoyl chloride in the above procedure.

EXAMPLE 7: Synthesis of Mixed Acyl/Ether Derivatives

The alkyl, acyl and mixture of acyl/alkyl derivatives with the same or different aliphatic carbon chain lengths of the above compounds can be synthesized by using known procedures of blocking the primary and or secondary alcohol of the starting materials.

For example, the 1-acyl, 2-alkyl analogue of the above compound was synthesized by benzylation of the primary hydroxyl group of 3-(dimethylamino)-1,2-propanediol (1.0) mol) with 0.9 mol of benzyl chloride to obtain a lyso compound which, on condensation with palmitic or oleic methansulfonate gave 1-O-alkyl, 2-O-benzyl-3-dimethylaminopropyl glycerol. Debenzylation followed by acylation of the resulting compound with palmitic acid chloride and quaternization under similar conditions as described above gave the required compound. The synthesis of alkyl/acyl analogues was achieved by two routes:

(a) 3-(dimethylamino)-1,2-propanediol (1.0 mol) was reacted with 0.7 mol of palmitic methanesulfonate to obtain 1-O-palmityl-2-lyso-3-dimethylaminopropyl glycerol. Acylation of the above lyso compound with oleic anhydride gave the alkyl/acyl derivative.

(b) The primary alcohol group of batyl alcohol (Serdary Research Laboratory) is protected with ts-Cl and NaI and the secondary hydroxyl group is then acylated with oleic anhydride to obtain alkyl/acyl iodohydrin derivative. Further treatment of the iodohydrin derivative with dimethyl amine gave the required product. These compounds are then quaternized by using the procedures described above.

EXAMPLE 8: 3,5-(N,N-di-lysyl)-diaminobenzoyl-3-(DL-1,2-dipalmitoyl-dimethylaminopropyl-β-hydroxyethylamine) (DLYS-DABA-DPRI diester)

Step 1: Di-t-Butyloxycarbonyl-3,5-di-aminobenzoic acid (Bis-Boc-DABA)

A quantity of 3,5-Di-aminobenzoic acid (1.52 g; 10 mmol), triethylamine (2.8 ml, 10 mmol) and di-t-butyl-di-carbonate (4.5 g; 22 mmol) (Aldrich Chemical Co, Milwaukee, Wis.), were dissolved in DMF (10 ml) and stirred for 24 hours at room temperature. The solvent was evaporated under vacuum and the product was chromatographed on silica gel using chloroform as eluent to obtain the title compound.

Step 2: Bis-Boc-DABA-DPRI diester

Bis-Boc DABA (3.52 g, 10 mmol) and DPRI (10 mmol) were coupled following the procedure described in procedures 7.3 and 7.4 above.

Step 3: 3,5-(NN-Di-lysyl)-DABA-DPRI diester

Compound #6 (2 mmol) was treated with TFA (10 ml) for 30 min at room temperature to remove the BOC protecting groups. After evaporating the solvent, the product was reacted with Bis-Boc-lysine (5 mmol) using DCC as condensing agent. The product isolated after evaporating the solvent was deprotected using TFA and purified as described in 7.4 above.

EXAMPLE 9: 3,5-(N,N-di-lysyl)-diaminobenzoyl-glycyl-3-(DL-1,2-dipalmitoyl-dimethylaminopropyl-β-hydroxyethylamine) (DLYS-DABA-GLY-DPRI diester)

Step 1: Di-t-Butyloxycarbonyl-3,5-di-aminobenzoic acid (Bis-Boc-DABA)

As in Example 7 above.

Step 2: Boc-glycyl-DPRI diester:

Boc-glycine (1.75 g, 10 mmol) and DPRI (10 mmol) were coupled following the procedure described in Steps 3 and 4 of Example 8.

Step 3: Bis-Boc-DABA-glycyl-DPRI diester:

Bis-Boc-DABA (3.52 g, 10 mmol) of the compound from Step 2 above was treated with TFA (10 ml) doe 30 min. at room temperature to remove the Boc protecting group. TFA was evaporated and the product was coupled with Bis-Boc-DABA from Step 1 above as described in Example 8.

Step 4: 3,5-(NN-Di-lysyl)-DABA-glycyl-DPRI diester

The compound from Step 3 above (2 mmol) was treated with TFA (10 ml) for 30 min. at room temperature to remove the BOC protecting groups. After evaporating the solvent, the product was reacted with Bis-Boc-lysine (5 mmol) using DCC as condensing agent. The product isolated after evaporating the solvent was deprotected using TFA and purified as described in Step 4 of Example 8.

Various DORI derivatives corresponding to the DPRI derivatives described in Examples 8 and 9 can be synthesized by substituting DORI in the coupling procedures.

EXAMPLE 10: Synthesis of L-spermine-5-carboxyl-3-(DL-1,2-dipalmitoyl-dimethylaminopropyl-$\beta$-hydroxyethylamine) (SPC-DPRI diester)

L-5-carboxytetrabutyloxycarbonylspermine (tetra-BOC-Sper-COOH) (664 mg; 1 mmol) prepared according to published procedures (J.-P. Behr et. al. *Proc. Natl. Acad. Sci., USA*, 86, pp 6982-6986, 1989) was coupled to DPRI (1 mmol) as described in 8.3. The product was de-protected and purified by chromatography to prepare SPC-DPRI diester.

EXAMPLE 11: PREPARATION OF LIPOSOME-FORMING DOTAP

The cationic liposome-forming material 1,2-bis-(oleoyloxy)-3-(trimethylammonio)propane (DOTAP) may be also prepared as reported by L. Stamatatos, et al. *Biochemistry* 27:3917-3925 (1988) or H. Eibl et al., *Biophysical Chemistry* 10:261-271 (1979).

Briefly, Stamatatos et al. report that 1 mmol of 3-bromo-1,2-propanediol (Aldrich, Milwaukee, Wis.) was acylated for 48 hours at 20° C. with 3 mmol of oleoyl chloride (freshly prepared from oleic acid and oxalyl chloride) in dry, alcohol-free diethyl ether (20 ml) containing 5 mmol of dry pyridine. The precipitate of pyridinium hydrochloride was filtered off, and the filtrate was concentrated under nitrogen and redissolved in 10 ml of hexane. The hexane solution was washed 3 times with an equal volume of 1:1 methanol/0.1N aqueous HCOONa, pH 3.0, 3 times with 1:1 methanol/0.1N aqueous NaOH, and 1 time with 1% aqueous NaCl. The crude 3-bromo-1,2-bis-(oleoyloxy)propane was then stirred for 72 hours in a sealed tube with a solution of 15% trimethylamine in dry dimethyl sulfoxide (30 ml) at 25° C. The products of this reaction were dissolved in chloroform (200 ml), which was repeatedly washed with 1:1 methanol/100 mM aqueous HCOONa, pH 3.0, and then evaporated in vacuo to yield a light yellow oil. The material was purified on a column of silicic acid (Bio-Sil A, Bio-Rad Laboratories), eluting with a 0-15% gradient of methanol in chloroform to give the desired product in pure form at 9-10% methanol.

This purified product was a colorless, viscous oil that migrates with an $R_f$ of 0.4 on thin layer chromatography plates (Silica Gel G) that were developed with 50:15:5:5:2 $CHCl_3$/acetone/$CH_3OH$/$CH_3COOH$/H.

EXAMPLE 12: LIPID VESICLE PREPARATION

Dioleoylphosphatidylcholine (DOPC), dioleoylphosphatidylglycerol (DOPG) and dioleoylphosphatidylethanolamine (DOPE) were purchased from Avanti Polar Lipids, (Pelham, Ala.). DOTMA was synthesized according to U.S. Pat. No. 4,897,355 to Epstein, D. et al. or Felgner, P. L. et al., PNAS 84: 7413-7417 (1987) and DOTAP was synthesized according to Example 10. DOPG/DOPC vesicles were prepared by drying 50 mg of DOPG and 50 mg of DOPC under a stream of nitrogen gas into a sonication vial. The sample was placed on a vacuum pump overnight and was hydrated the following day with deionized water to a concentration of 10 mg/ml total lipid. The sample was sonicated for 2 hours in the capped vial, using the Heat Systems model 350 sonicator equipped with an inverted cup (bath type) probe at the maximum setting and the bath was circulated at 15° C. Alternatively, negatively charged vesicles can be prepared without sonication to produce multilamellar vesicles (MLV) or by extrusion through nuclepore membranes to produce unilamellar vesicles of a discrete size. Other methods are also available and are known to those familiar with the art. DOTMA or DOTAP vesicles were prepared in an exactly analogous manner.

EXAMPLE 13: POLYNUCLEOTIDE/CATIONIC LIPID COMPLEX FORMATION

Polynucleotide complexes were prepared by mixing 0.5 ml of a 10 ug/ml polynucleotide solution with 0.5 ml of sonicated DOTMA/PE or DOTAP/PE liposomes at 40-100 ug/ml by slow addition through a syringe with constant gentle vortexing. The diluted polynucleotide and liposome solutions are prepared from concentrated stock solutions by dilutions into Opti-MEM Reduced Serum Media obtained from Gibco/BRL, Gaithersburg, Md., at room temperature. This procedure results in positively charged complexes which will spontaneously deliver polynucleotide into cells in tissue culture. Different ratios of positively charged liposomes to polynucleotides can be used to suit the need. These methods are essentially as described in Felgner, P. L. et al., PNAS 84: 7413-7417 (1987), and Felgner, P. and M. Holm, Focus 11(2) Spring, 1989.

EXAMPLE 14: TRANSFECTION PROTOCOLS

A: General Protocol

Transfections of RNA according to Examples 15-19 were carried out as follows:

Plates (10 cm) of rapidly dividing adherent cells near confluency, or $1 \times 10^7$ suspension cells, were transfected as follows unless otherwise noted. Cells were washed once in Opti-MEM Reduced Serum Medium (Gibco) and then returned to the incubator covered in Opti-MEM. Aliquots (4 ml) of Opti-MEM Medium were placed in $12 \times 75$ mm polystyrene snap cap tubes, and 50 ug of Lipofectin Reagent were added. A mixture of capped mRNA and uncapped carrier RNA transcribed from EcoR V-linearized pIBI31 (according to Malone, R. et al., *Proc. Nat'l Acad. Sci. USA* 86:6077-6081 (1989)) was then added to the media/lipid mixture to a total of 20 ug of RNA. The mixture was immediately vortexed. Cells were removed from the incubator, the medium removed, and the Opti-MEM/lipid/RNA mixture added. Cells were then returned to the incubator for 8 h, unless otherwise noted, and harvested as described.

Murine fibroblasts (NIH 3T3, clone 2B) cells were maintained in Dulbecco's Modified Eagles Medium, (DMEM)+10% (v/v) calf serum (CS) prior to transfection.

B: 96-well microwell plate procedure

The RNA transfection according to Example 20 and the DNA transfections according to Examples 20-23 were carried out in 96-well plates, as follows:

(1) The wells of a 96-well microtiter plate were seeded with 20,000 to 40,000 cells per well;

(2) Dilutions of cationic lipid preparations and polynucleotide preparations from stock solutions were carried out by 2-dimensional serial dilutions in two separate 96-well plates according to the scheme set forth in the Table below;

(3) Corresponding dilutions of lipid and polynucleotide were mixed by transferring an equal volume of polynucleotide to a corresponding lipid microwell;

(4) The serum-containing media was evaporated from the wells containing the cells;

(5) A quantity of about 100 μl of the cationic lipid/DNA complexes were added to cells in each well of the microtiter plate. Final dilutions and molar ratios of lipid and polynucleotide in each well are indicated in the Table below.

(6) The plates were incubated at 37° C. (5% $CO_2$). At 4-24 hours post transfection, an aliquot of 10% serum in Optimem ™ was added to each well;

(7) At the end of the incubation, the assay media of the cells or a whole cell lysate was assayed for expression activity.

Where beta-glactosidase was the reporter gene, the expression was monitored colorimetrically, using 2-nitrophenyl-$\beta$-D-galactopyranoside (ONPG) or chlorophenyl red-$\beta$-D-galactopyranoside (CPRG) as a substrate, reading the plates with a microtiter reader at 405 nm.

---

Transfection Protocol in vitro

Cationic Lipid Plate Preparation
Cationic lipid (nmole/ml: uM)
2× serial dilution in microliter plate

|   | 1 | 2 | 3 | 4 | 5 | 6 | 7 | 8 |
|---|---|---|---|---|---|---|---|---|
| A | 672.14 | 336.07 | 168.04 | 83.54 | 41.37 | 21.04 | 10.44 | 5.23 |
| B | 672.14 | 336.07 | 168.04 | 83.54 | 41.37 | 21.04 | 10.44 | 5.23 |
| C | 672.14 | 336.07 | 168.04 | 83.54 | 41.37 | 21.04 | 10.44 | 5.23 |
| D | 672.14 | 336.07 | 168.04 | 83.54 | 41.37 | 21.04 | 10.44 | 5.23 |
| E | 672.14 | 336.07 | 168.04 | 83.54 | 41.37 | 21.04 | 10.44 | 5.23 |
| F | 672.14 | 336.07 | 168.04 | 83.54 | 41.37 | 21.04 | 10.44 | 5.23 |
| G | 672.14 | 336.07 | 168.04 | 83.54 | 41.37 | 21.04 | 10.44 | 5.23 |
| H | 672.14 | 336.07 | 168.04 | 83.54 | 41.37 | 21.04 | 10.44 | 5.23 |

Polynucleotide Plate Preparation
Polynucleotide (nmole/ml: uM)
2× serial dilution in microliter plate

|   | 1 | 2 | 3 | 4 | 5 | 6 | 7 | 8 |
|---|---|---|---|---|---|---|---|---|
| A | 242.42 | 242.42 | 242.42 | 242.42 | 242.42 | 242.42 | 242.42 | 242.42 |
| B | 121.21 | 121.21 | 121.21 | 121.21 | 121.21 | 121.21 | 121.21 | 121.21 |
| C | 60.61 | 60.61 | 60.61 | 60.61 | 60.61 | 60.61 | 60.61 | 60.61 |
| D | 30.30 | 30.30 | 30.30 | 30.30 | 30.30 | 30.30 | 30.30 | 30.30 |
| E | 15.15 | 15.15 | 15.15 | 15.15 | 15.15 | 15.15 | 15.15 | 15.15 |
| F | 7.58 | 7.58 | 7.58 | 7.58 | 7.58 | 7.58 | 7.58 | 7.58 |
| G | 3.79 | 3.79 | 3.79 | 3.79 | 3.79 | 3.79 | 3.79 | 3.79 |
| H | 1.89 | 1.89 | 1.89 | 1.89 | 1.89 | 1.89 | 1.89 | 1.89 |

Mix Plate
(by transferring equal volume of Polynucleotide to Lipid)

↓

+/− Serum
(adding opti-mem or serum containing opti-mem)

Final Concentrations of Cationic Lipid and Polynucleotide prior transfection; and their Molar Ratio Cationic Lipid (nmole/ml): 2× serial dilution columnwise

| Polynucleotide (nmole/ml): 2× serial dil rowwise | | 1 | 2 | 3 | 4 | 5 | 6 | 7 | 8 | |
|---|---|---|---|---|---|---|---|---|---|---|
| | A | 168.00 | 84.00 | 42.00 | 21.00 | 10.50 | 5.25 | 2.63 | 1.32 | [Lipid] (uM) |
| | | 60.60 | 60.60 | 60.60 | 60.60 | 60.60 | 60.60 | 60.60 | 60.60 | [MA] (uM) |
| | | 2.77 | 1.39 | 0.69 | 0.35 | 0.17 | 0.09 | 0.04 | 0.02 | L/M racie |
| | B | 168.00 | 84.00 | 42.00 | 21.00 | 10.50 | 5.25 | 2.63 | 1.32 | [Lipid] (uM) |
| | | 30.30 | 30.30 | 30.30 | 30.30 | 30.30 | 30.30 | 30.30 | 30.30 | [MA] (uM) |
| | | 5.55 | 2.77 | 1.39 | 0.69 | 0.35 | 0.17 | 0.09 | 0.04 | L/M racie |
| | C | 168.00 | 84.00 | 42.00 | 21.00 | 10.50 | 5.25 | 2.63 | 1.32 | [Lipid] (uM) |
| | | 15.15 | 15.15 | 15.15 | 15.15 | 15.15 | 15.15 | 15.15 | 15.15 | [MA] (uM) |
| | | 11.09 | 5.55 | 2.77 | 1.39 | 0.69 | 0.35 | 0.17 | 0.09 | L/M racie |
| | D | 168.00 | 84.00 | 42.00 | 21.00 | 10.50 | 5.25 | 2.63 | 1.32 | [Lipid] (uM) |
| | | 7.57 | 7.57 | 7.57 | 7.57 | 7.57 | 7.57 | 7.57 | 7.57 | [MA] (uM) |
| | | 22.19 | 11.09 | 5.55 | 2.77 | 1.39 | 0.69 | 0.35 | 0.17 | L/M racie |
| | E | 168.00 | 84.00 | 42.00 | 21.00 | 10.50 | 5.25 | 2.63 | 1.32 | [Lipid] (uM) |
| | | 3.79 | 3.79 | 3.79 | 3.79 | 3.79 | 3.79 | 3.79 | 3.79 | [MA] (uM) |
| | | 4.33 | 22.19 | 11.09 | 5.55 | 2.77 | 1.39 | 0.69 | 0.35 | L/M racie |
| | F | 168.00 | 84.00 | 42.00 | 21.00 | 10.50 | 5.25 | 2.63 | 1.32 | [Lipid] (uM) |
| | | 1.90 | 1.90 | 1.90 | 1.90 | 1.90 | 1.90 | 1.90 | 1.90 | [MA] (uM) |
| | | 88.42 | 44.33 | 22.19 | 11.09 | 5.55 | 2.77 | 1.39 | 0.69 | L/M racie |

-continued
Transfection Protocol in vitro

| | | | | | | | | | |
|---|---|---|---|---|---|---|---|---|---|
| G | 168.00 | 84.00 | 42.00 | 21.00 | 10.50 | 5.25 | 2.63 | 1.32 | [Lipid] (uM) |
| | 0.95 | 0.95 | 0.95 | 0.95 | 0.95 | 0.95 | 0.95 | 0.95 | [MA] (uM) |
| | 176.84 | 88.42 | 44.33 | 22.19 | 11.05 | 5.55 | 2.77 | 1.39 | L/M racie |
| H | 168.00 | 84.00 | 42.00 | 21.00 | 10.00 | 5.25 | 2.63 | 1.32 | [Lipid] (uM) |
| | 0.48 | 0.48 | 0.48 | 0.48 | 0.48 | 0.48 | 0.48 | 0.48 | [MA] (uM) |
| | 353.68 | 176.84 | 88.42 | 44.33 | 22.19 | 11.09 | 5.55 | 2.77 | L/M racie |

↓

Add Lipid/Polynucleotide Mixture to Plate containing Cells

EXAMPLE 15: DEMONSTRATION OF THE SERUM INHIBITORY EFFECT

Luciferase RNA expression was determined in 3T3 cells following cationic lipid mediated transfection, according to the procedure described in Example 14, in the presence of increasing concentrations of fetal bovine serum. The transfection formulation consisted of luciferase mRNA (HYCLONE) in a lipid mixture comprising 80% DOTMA and 20% DOPE. In carrying out the transfections, serum was added to both the cationic lipid solution and the RNA stock solutions prior to mixing the lipid and the RNA.

The data below, plotted as FIG. 1, shows the marked inhibitory effect of serum on transfection.

| Percent Serum | Luciferase Activity |
|---|---|
| 0 | 1716 |
| 5 | 71.1 |
| 10 | 47.0 |
| 15 | 35.6 |
| 20 | 29.9 |
| Control | 13.9 |

EXAMPLE 16: TWO-STAGE PROTOCOL TO OPPOSE THE SERUM INHIBITORY EFFECT

In an experiment subsequent to that described in Example 15, the procedure was identical except that DOTMA:DOPE 80:20 was mixed with the mRNA solution before the addition of serum. The data below and in FIG. 2 show a marked transfection-enhancing effect at low serum concentrations. Note the difference in y-axis scales in FIGS. 1 and 2.

| Incubation (minutes) | Serum: | | | |
|---|---|---|---|---|
| | None | 5% | 15% | 20% |
| 0 | 1716 | 15465 | 6175 | 2497 |
| 5 | 2136 | 15285 | 7335 | 2368 |
| 10 | 1751 | 12490 | 4696 | 2294 |
| 20 | 1345 | 12110 | 3929 | 2133 |

EXAMPLE 17: OPTIMIZATION OF CATIONIC LIPID MEDIATED TRANSFECTION

A total of 24 cationic lipid vesicle formulations were prepared using either DOTMA or DOTAP as the cationic lipid species (CL). The effect of charge density was evaluated by increasing the mole % of the cationic lipid species relative to a neutral phospholipid, either dioleoyl phosphatidyl ethanolamine (DOPE) or dioleoyl phosphatidyl choline (DOPC). Each formulation was prepared with and without 33 mole % cholesterol. Four different levels of lipid were tested: 50, 75, 100, and 125 μg; at a fixed RNA level of 20 μg total, comprised of 5μg luciferase message and 15 μg ribosomal RNA. The levels of expression, including the peak level at the optimum lipid concentration, are listed below and plotted in FIG. 3.

| Mole percent | CL:CL + Phospholipid | Luciferase light units | | |
|---|---|---|---|---|
| | | 20% | 50% | 80% |
| DOPE | DOTMA | 86 | 830 | 4268 |
| | DOTAP | 1 | 536 | 1066 |
| | DOTMA:Cholesterol 7:3 | 127 | 1102 | 1568 |
| | DOTAP:Cholesterol 7:3 | 2 | 77 | 784 |
| DOPC | DOTMA | 2 | 51 | 69 |
| | DOTAP | 2 | 3 | 51 |
| | DOTMA:Cholesterol 7:3 | 48 | 522 | 501 |
| | DOTAP:Cholesterol 7:3 | 0 | 88 | 256 |

These data identify several critical formulation issues that are important for optimal activity:

(1) The inclusion of neutral phospholipids in CL vesicle formulations reduce functional activity and expression of mRNA.

(2) DOPC has a greater inhibitory effect than DOPE.

(3) DOTMA (a diether compound) is more active than DOTAP (the corresponding diester compound).

(4) Cholesterol does not have a dramatic inhibitory effect in these formulations.

EXAMPLE 18: EFFECTIVENESS OF TRANSFECTION FORMULATIONS LACKING NEUTRAL PHOSPHOLIPIDS

Since the data of Example 17 indicated that formulations containing increasing quantities of a neutral phospholipid (DOPE or DOPC) are increasingly less active, some alternative formulations lacking the neutral phospholipid component were tested. Four different levels of lipid were tested: 50, 75, 100, and 125 μg; at a fixed RNA level of 20 μg total, comprised of 5μg luciferase message and 15μg ribosomal RNA. The levels of expression, including the peak level at the optimum lipid concentration, are listed below and plotted in FIG. 4. The data indicates that formulations consisting of either 100 mole % DOTMA or 70 mole % DOTMA and 30 mole % cholesterol give rise to the highest activity in the absence of serum. Data below indicate that the best activity in the presence of serum occurs with the formulations containing cholesterol. For example, the replacement of 30% of the DOTMA in 100/0/0 by cholesterol in the formulation 70/0/30 demonstrates marked enhancement of activity due to the presence of cholesterol.

| Formulation DOTMA/PL/CHOL | Total Lipid (μg) | Luciferase Light Units | |
|---|---|---|---|
| | | 10% Serum | Opti-MEM |
| 50/50/0 | 50 | 1217 | 568 |

-continued

| Formulation DOTMA/PL/CHOL | Total Lipid (μg) | Luciferase Light Units 10% Serum | Opti-MEM |
|---|---|---|---|
| | 75 | 1309 | 176 |
| | 100 | 1047 | 96 |
| | 125 | 923 | 39 |
| 80/20/0 | 50 | 1510 | 450 |
| | 75 | 1347 | 215 |
| | 100 | 1469 | 81 |
| | 125 | 1046 | 55 |
| 100/0/0 | 50 | 208 | 2908 |
| | 75 | 53 | 939 |
| | 100 | 63 | 590 |
| | 125 | 50 | 196 |
| 35/35/30 | 50 | 585 | 1716 |
| | 75 | 739 | 543 |
| | 100 | 1491 | 240 |
| | 125 | 1421 | 160 |
| 56/14/30 | 50 | 1531 | 875 |
| | 75 | 1251 | 1146 |
| | 100 | 1355 | 964 |
| | 125 | 1007 | 500 |
| 70/0/30 | 50 | 3788 | 2415 |
| | 75 | 891 | 1674 |
| | 100 | 323 | 784 |
| | 125 | 185 | 367 |

EXAMPLE 19: STRUCTURE-TRANSFECTION ACTIVITY OF CATIONIC LIPIDS

To compare the effect of various structural modifications on the transfection activity demonstrated by cationic lipids, formulations containing DOTMA, DPTMA, DPRI diester and DORI diester were prepared as described in the preceding examples and used in the transfection of tissue culture cells with RNA coding for the luciferase enzyme as described in Example 14A. DOTMA is the cationic lipid found in Lipofectin TM. However, in this experiment, all lipid formulations were prepared with 70 mole % cationic lipid and 30 mole % cholesterol, a ratio which is shown to make the DOTMA formulation used herein 3-4 fold more active than the Lipofectin TM reagent (See Example 17 and FIG. 4). A range of lipid from 0.012 to 0.300 μg were used to transfect a fixed amount of RNA, comprising 5 μg luciferase message and 15 μg ribosomal RNA. The results are indicated in the data below and also in FIG. 5.

| μM Lipid | DORI | DOTMA | DPRI | DPTMA |
|---|---|---|---|---|
| 0.012 | 30 | 26 | 54 | 16 |
| 0.025 | 62 | 91 | 284 | 17 |
| 0.050 | 248 | 554 | 467 | 24 |
| 0.075 | 640 | 1555 | 404 | 36 |
| 0.100 | 1541 | 3901 | 160 | 53 |
| 0.125 | 2933 | 4662 | 272 | 65 |
| 0.150 | 5906 | 6368 | 413 | 114 |
| 0.175 | 9216 | 6772 | 899 | 145 |
| 0.200 | 12115 | 6757 | 1959 | 190 |
| 0.225 | 11705 | 6491 | 2124 | 218 |
| 0.250 | 10230 | 6572 | 2329 | 289 |
| 0.275 | 9885 | 5616 | 2339 | 336 |
| 0.300 | 7947 | 3651 | 1995 | 479 |

The relative activities of the analogues is shown to be DORI>DOTMA>DPRI>DPTMA. The commercially available Rosenthal Inhibitor (RI) was tested and found to have very weak activity (data not shown); however, the dipalmitoyl derivative (DPRI diester) was several times more active than the corresponding dipalmitoyl derivative of DOTMA (DPTMA). It was for this reason the dioleoyl derivative of the Rosenthal inhibitor was synthesized, and it was found to be more active than DOTMA. Based on this analysis, quaternization of the DOTMA derivatives with the hydroxyethyl moiety present in RI will further improve the activity of the cationic lipids.

The structure activity relationships indicated by this data are:

(1) Ether>Ester aliphatic group linkages
(2) Unsaturated>Saturated aliphatic groups
(3) Hydroxyethyl>Methyl quaternizing groups These data indicate that cationic lipids can be made that differ substantially with respect to transfection activity and that some analogs are more active than DOTMA. Note particularly that the DOTMA formulation here and shown on FIG. 5 is much more active than the commercial Lipofectin TM standard.

EXAMPLE 20: Effect of Lyso Lipids in Increasing the Effectiveness of Transfection Formulations The in vitro transfection efficiency of lipid formulations containing lysophosphatidylcholine (1-oleoyl lysophosphatidylcholine) in DOTMA/DOPE (Lipofectin TM) was evaluated by the gene expression of beta-galactosidase from pSV2-lacZ plasmid in COS.7 cells.

Transfection Protocol

A population of 20,000 cells was transfected in microwell plate wells using the quantities of lipid and DNA indicated in Example 14A and in the absence of serum. DNA (β-galactosidase; pSV2LacZ) and transfection lipid formulations of Lipofectin TM and Lipofectin TM and lysophosphatidylcholine were prepared as serial dilutions from stock solutions (DNA: 160 μg/ml; Lipids: 0.747 mM)in Optimem TM in 96-well plates, and the corresponding dilutions mixed together. A quantity of 100 ml of the DNA-lipid mixture was added to each microtiter well containing about 20,000 COS.7 cells aspirated free of fluid. The plate was incubated at 37° C. (5% CO2) for 4 hours, at which time 50 ml of 30% bovine serum in Optimem TM was added to each well to yield a serum concentration of 10%. After an additional 24 hours of incubation at 37° C., a volume of 100 ml of 10% bovine calf serum in Optimem TM was added to each well and the incubation continued for another 24 hours at 37° C. After 48 hours, the transfection reagent was aspirated and 50 μl of lysis buffer (0.1% triton-X100 in 250 mM Tris, pH 8) was added to each well. The plate was frozen at −70° C. and subjected to 3 freeze-thaw cycles between −70° C. and room temperature. A quantity of 50 μl of PBS (containing 0.5% BSA) was added to each well, followed by an addition of 150 μl of a β-galactosidase substrate ONPG at a concentration of 2 mg/ml. Absorbance at 405 nm was read from a standard curve. To compare the effect of various structural modifications on the transfection activity demonstrated by cationic lipids, formulations containing DOTMA, DPTMA, DPRI diester and DORI diester were prepared as described in the preceding examples and used in the transfection of tissue culture cells with RNA coding for the luciferase enzyme as described in Example 14A. DOTMA is the cationic lipid found in Lipofectin TM. The following four formulations were tested:

| Composition | Molar Ratios | |
|---|---|---|
| DOTMA/DOPE/LysoPC | 5/5/0 | (1/1/0) |
| DOTMA/DOPE/LysoPC | 5/5/1.25 | (1/1/.25) |

-continued

| Composition | Molar Ratios | |
|---|---|---|
| DOTMA/DOPE/LysoPC | 5/5/2.5 | (1/1/.5) |
| DOTMA/DOPE/LysoPC | 5/5/5 | (1/1/1) |

RESULTS

Experimental results are summarized in the following tables. Data represent pg expression of β-galactosidase.

DOTMA/DOPE/LysoPC 1/1/0 (5/5/0)

| DNA (pmole) | Cationic lipid (pmole) | | | | | | | |
|---|---|---|---|---|---|---|---|---|
| | 16800 | 8400 | 4200 | 2100 | 1050 | 525 | 262.5 | 131 |
| 6060 | −56.9 | 211.7 | 778.7 | 1171.9 | 1098.6 | 667.2 | 433.8 | 255.4 |
| 3030 | −63.3 | 32.9 | 351.1 | 1390.6 | 1175.7 | 776.1 | 386.3 | 167.2 |
| 1515 | −67.1 | −49.3 | 69.4 | 734.6 | 1265.1 | 738.0 | 346.9 | 168.1 |
| 758 | −66.2 | −49.7 | −23.0 | 519.4 | 437.6 | 635.5 | 352.8 | 130.8 |
| 379 | −73.0 | −52.2 | −45.9 | 265.6 | 163.0 | 300.7 | 316.4 | 140.6 |
| 189 | −75.6 | −49.7 | −57.8 | 133.3 | 58.3 | 177.8 | 252.0 | 174.4 |
| 95 | −76.0 | −73.4 | −57.3 | 18.5 | 30.0 | 68.1 | 97.3 | 152.0 |
| 47 | −72.6 | −69.2 | −54.4 | −20.9 | 8.8 | 27.0 | 68.1 | 81. |

DOTMA/DOPE/Lyso PC 1/1/0.25 (5/5/1.25)

| DNA (pmole) | Cationic lipid (pmole) | | | | | | | |
|---|---|---|---|---|---|---|---|---|
| | 16800 | 8400 | 4200 | 2100 | 1050 | 525 | 262.5 | 131 |
| 6060 | −111.7 | −22.4 | 1039.5 | 1678.2 | 1801.4 | 1202.0 | 445.7 | 160.0 |
| 3030 | −122.9 | −66.9 | 244.0 | 1602.5 | 2101.1 | 1658.6 | 493.3 | 611.0 |
| 1515 | −134.1 | −122.9 | 129.2 | 787.4 | 1801.4 | 1563.3 | 711.8 | 571.7 |
| 758 | −128.5 | −111.7 | −103.3 | 529.7 | 809.8 | 1588.5 | 793.0 | 468.1 |
| 379 | −122.9 | −125.7 | −117.3 | 230.0 | 440.1 | 611.0 | 711.8 | 196.4 |
| 189 | −142.5 | −145.4 | −131.3 | 89.9 | 188.0 | 213.2 | 314.0 | 120.8 |
| 95 | −125.7 | −153.8 | −128.5 | −47.3 | 78.7 | 426.1 | 179.6 | 126.4 |
| 47.4 | −139.7 | −145.4 | −103.3 | −64.1 | 358.9 | 123.6 | 78.7 | 89.9 |

DOTMA/DOPE/Lyso PC 1/1/0.5 (5/5/2.5)

| DNA (pmole) | Cationic lipid (pmole) | | | | | | | |
|---|---|---|---|---|---|---|---|---|
| | 16800 | 8400 | 4200 | 2100 | 1050 | 525 | 262.5 | 131 |
| 6060 | −10.2 | 53.4 | 446.6 | 237.4 | 355.8 | 765.0 | 593.0 | 269.0 |
| 3030 | −53.8 | 4.6 | 211.0 | 1025.8 | 374.6 | 613.4 | 394.6 | 273.4 |
| 1515 | −58.2 | −36.2 | 281.8 | 772.2 | 877.0 | 672.6 | 679.8 | 282.2 |
| 758 | −65.4 | −55.4 | 121.8 | 505.0 | 728.2 | 1284.2 | 667.8 | 371.0 |
| 379 | −68.2 | −71.8 | 32.2 | 320.2 | 185.4 | 544.2 | 1002.2 | 325.0 |
| 189 | −69.0 | −73.0 | −23.0 | 179.0 | 228.2 | 221.8 | 375.4 | 284.2 |
| 95 | −71.0 | −73.0 | −42.6 | 68.6 | 45.4 | 157.8 | 219.4 | 84.6 |
| 47.4 | −70.6 | −70.6 | −21.4 | 33.0 | 69.4 | 41.8 | 75.8 | 75.8 |

DOTMA/DOPE/LysoPC 1/1/1 (5/5/5)

| DNA (pmole) | Cationic lipid (pmole) | | | | | | | |
|---|---|---|---|---|---|---|---|---|
| | 16800 | 8400 | 4200 | 2100 | 1050 | 525 | 262.5 | 131 |
| 6060 | 55.6 | 190.0 | 381.7 | 156.0 | 64.7 | 9.0 | 95.5 | 152.1 |
| 3030 | −47.2 | 98.7 | 341.4 | 752.8 | 114.9 | 67.5 | 250.9 | 187.2 |
| 1515 | −59.4 | 44.9 | 267.9 | 652.8 | 468.3 | 50.5 | 115.3 | 170.2 |
| 758 | −65.7 | −30.9 | 199.9 | 537.8 | 765.5 | 169.8 | 130.3 | 208.6 |
| 379 | −62.6 | −39.6 | 110.2 | 466.7 | 275.0 | 544.5 | 219.6 | 271.0 |
| 189 | −72.8 | −51.1 | 19.2 | 306.2 | 199.5 | 352.1 | 483.3 | 273.0 |
| 95 | −74.0 | −65.7 | −13.6 | 123.6 | 168.7 | 166.3 | 158.4 | 218.1 |
| 47.4 | −75.2 | −57.8 | −32.1 | 77.0 | 95.1 | 69.4 | 155.2 | 143.4 |

EXAMPLE 21: COMPARATIVE TRANSFECTION EFFICIENCY OF CATIONIC LIPID ANALOGS

Cationic lipid formulations comprising DOTMA/DOPE 5/5, DORI/DOPE 5/5, and DORIE/DOPE 5/5 were used to transfect COS.7 cells at a density of 40,000 cells per well according to the procedure of Example 14B. As indicated Figure and in the Table below, DORI and DORIE analogs show superior transfection activity compared to DOTMA. No significant difference in effectiveness was seen between cationic lipid having ester linkages and ether linkages (DORI compared to DORIE). However, the hydroxyethyl moiety linked to the nitrogen of quaternary ammonium (DORI and DORIE) appears to improve activity as compared to the methyl group of DOTMA.

DOTMA/DOPE (5/5)

| DNA (pmole) | Cationic lipid (pmole) | | | | | | | |
|---|---|---|---|---|---|---|---|---|
| | 16800 | 8400 | 4200 | 2100 | 1050 | 525 | 262.5 | 131 |
| 6060 | −200.0 | 326.1 | 1764.1 | 1450.3 | 571.2 | 375.2 | 22.2 | −20.3 |
| 3030 | −291.5 | −332.7 | 1012.4 | 744.4 | 509.2 | 139.9 | 28.8 | −23.5 |
| 1515 | −304.6 | 48.4 | 702.0 | 398.0 | 499.3 | 215.0 | 58.2 | 48.4 |
| 758 | −275.2 | −186.9 | 577.8 | 385.0 | 293.5 | 110.5 | 45.1 | 28.8 |
| 379 | −317.6 | −262.1 | 120.3 | 221.6 | 286.9 | 123.5 | 45.1 | 45.1 |
| 189 | −324.2 | −294.8 | 28.8 | 179.1 | 139.9 | −66.0 | 68.0 | 19.0 |
| 95 | −327.5 | −298.0 | −141.2 | 205.2 | 130.1 | 136.6 | 19.0 | −0.7 |
| 47.4 | −311.1 | −324.2 | −26.8 | 126.8 | −26.8 | 126.8 | −13.7 | 28.8 |

DORI/DOPE (5/5)

| DNA (pmole) | Cationic lipid (pmole) | | | | | | | |
|---|---|---|---|---|---|---|---|---|
| | 16800 | 8400 | 4200 | 2100 | 1050 | 525 | 262.5 | 131 |
| 6060 | 1321.4 | 1289.1 | 2111.7 | 1611.7 | 906.0 | 466.5 | 285.1 | 87.5 |
| 3030 | 853.6 | 1289.1 | 1958.5 | 1559.3 | 1079.4 | 502.8 | 321.4 | 293.1 |
| 1515 | 906.0 | 1781.0 | 1773.0 | 1724.6 | 680.2 | 252.8 | 184.3 | 139.9 |
| 758 | 563.3 | 708.5 | 833.5 | 1281.0 | 700.4 | 418.1 | 248.8 | 220.6 |
| 379 | 410.1 | 942.3 | 139.9 | 329.4 | 635.9 | 256.9 | 309.3 | 297.2 |
| 189 | −190.7 | 510.9 | 180.2 | 139.9 | 277.0 | 87.5 | 111.7 | 14.9 |
| 95 | −198.8 | −37.5 | 107.7 | 91.5 | 63.3 | 252.8 | 14.9 | 152.0 |
| 47.4 | −279.4 | −33.5 | 144.0 | 35.1 | 35.1 | 107.7 | 87.5 | 27.0 |

DORIE/DOPE (5/5)

| DNA (pmole) | Cationic lipid (pmole) | | | | | | | |
|---|---|---|---|---|---|---|---|---|
| | 16800 | 8400 | 4200 | 2100 | 1050 | 525 | 262.5 | 131 |
| 6060 | −67.3 | 1134.1 | 2040.3 | 1682.7 | 1352.8 | 415.3 | 92.4 | 290.3 |
| 3030 | −209.7 | 1349.4 | 1752.2 | 1856.3 | 981.3 | 380.6 | 148.0 | 61.2 |
| 1515 | −174.9 | 293.8 | 1904.9 | 2123.7 | 1321.6 | 387.6 | 328.5 | 106.3 |
| 758 | −178.4 | 151.5 | 700.1 | 1175.8 | 1526.5 | 516.0 | 120.2 | 68.1 |
| 379 | −174.9 | −60.3 | 179.2 | 196.6 | 453.5 | 339.0 | 193.1 | −15.2 |
| 189 | −265.2 | −147.2 | −39.5 | −29.1 | 325.1 | 134.1 | 50.8 | −4.8 |
| 95 | −147.2 | −105.5 | −112.4 | 144.5 | −4.8 | 266.0 | 71.6 | −46.5 |
| 47.4 | −109.0 | −251.3 | −49.9 | 245.2 | −60.3 | −46.5 | −63.8 | −29.1 |

EXAMPLE 22: EFFECT OF NEUTRAL LIPIDS IN THE TRANSFECTION FORMULATION ON EFFICIENCY OF TRANSFECTION

A. Neutral Phospholipid

Increasing concentrations of dioleoylphosphatidylethanolamine (DOPE) were added to DORI and the lipid formulation used to transfect COS.7 cells at a density of 20,000 cells/well with pSV2-lacZ according to the procedure of Example 14B. The formulation were evaluated for their comparative transfective efficiency by the expression of β-galactosidase activity as indicated in FIG. 8 and the Tables below:

DORI/DOPE (10/0)

| DNA (pmole) | Cationic lipid (pmole) | | | | | | | |
|---|---|---|---|---|---|---|---|---|
| | 16800 | 8400 | 4200 | 2100 | 1050 | 525 | 262.5 | 131 |
| 6060 | 240.8 | 496.5 | 905.5 | 558.7 | 197.4 | 80.3 | 35.5 | 22.5 |
| 3030 | −45.4 | 600.6 | 1389.6 | 954.6 | 239.3 | 133.8 | 44.2 | 22.5 |
| 1515 | −109.0 | 232.1 | 947.4 | 888.2 | 253.8 | 19.7 | 39.9 | 50.0 |
| 758 | −123.4 | −85.8 | 376.6 | 229.2 | 323.1 | 112.1 | 156.9 | 24.0 |
| 379 | −101.7 | −81.5 | 44.2 | 96.2 | 219.1 | 130.9 | 38.4 | 31.2 |
| 189 | −126.3 | −94.5 | −6.4 | 45.7 | 139.6 | 133.8 | 29.8 | 31.2 |
| 95 | −100.3 | −101.7 | −55.5 | 73.1 | 52.9 | 44.2 | 6.6 | 6.6 |
| 47 | −113.3 | −114.7 | −15.0 | −38.2 | 15.3 | −4.9 | −6.4 | 5.2 |

DORI/DOPE (8/2)

| DNA (pmole) | Cationic lipid (pmole) | | | | | | | |
|---|---|---|---|---|---|---|---|---|
| | 16800 | 8400 | 4200 | 2100 | 1050 | 525 | 262.5 | 131 |
| 6060 | 51.2 | 202.8 | 216.0 | 144.8 | 84.7 | 77.4 | 66.1 | 39.9 |
| 3030 | 107.3 | 287.1 | 88.6 | 81.2 | 107.3 | 53.0 | 49.3 | 47.4 |
| 1515 | 30.6 | 429.4 | 139.2 | 109.2 | 39.9 | 62.4 | 45.5 | 77.4 |
| 758 | 51.2 | 408.8 | 245.9 | 313.3 | 105.5 | 60.5 | 30.6 | 47.4 |
| 379 | 79.3 | 180.4 | 171.0 | 195.4 | 75.5 | 215.1 | 86.7 | 64.3 |
| 189 | 28.7 | 3.1 | 36.2 | 182.2 | 64.3 | 38.1 | 75.5 | 103.6 |

-continued

| | DORI/DOPE (8/2) | | | | | | | |
|---|---|---|---|---|---|---|---|---|
| | Cationic lipid (pmole) | | | | | | | |
| DNA (pmole) | 16800 | 8400 | 4200 | 2100 | 1050 | 525 | 262.5 | 131 |
| 95 | −46.2 | −20.0 | 0.6 | 30.6 | −29.4 | 21.2 | 51.2 | 6.2 |
| 47 | 13.7 | 24.9 | −38.7 | 30.6 | −16.3 | −25.6 | 34.3 | −3.1 |

| | DORI/DOPE (5/5) | | | | | | | |
|---|---|---|---|---|---|---|---|---|
| | Cationic lipid (pmole) | | | | | | | |
| DNA (pmole) | 16800 | 8400 | 4200 | 2100 | 1050 | 525 | 262.5 | 131 |
| 6060 | 341.5 | 876.6 | 1095.7 | 1543.8 | 1470.2 | 854.8 | 518.7 | 234.4 |
| 3030 | −63.2 | 640.8 | 819.7 | 1497.0 | 1640.8 | 908.4 | 490.3 | 425.1 |
| 1515 | −105.0 | 378.3 | 1075.6 | 1890.0 | 1189.3 | 741.1 | 505.2 | 232.8 |
| 758 | −111.7 | 112.4 | 572.2 | 1478.6 | 1515.4 | 637.5 | 591.0 | 247.8 |
| 379 | −110.0 | −3.0 | 336.5 | 766.2 | 744.5 | 998.7 | 667.6 | 239.5 |
| 189 | −106.7 | −41.5 | 134.1 | 366.6 | 293.0 | 384.9 | 369.9 | 192.6 |
| 95 | −105.0 | −63.2 | 42.1 | 155.9 | 130.8 | 219.4 | 289.6 | 276.3 |
| 47 | −110.0 | −13.0 | −11.4 | 150.8 | 77.3 | 122.4 | 67.2 | 35.5 |

| | DORI/DOPE (2/8) | | | | | | | |
|---|---|---|---|---|---|---|---|---|
| | Cationic lipid (pmole) | | | | | | | |
| DNA (pmole) | 16800 | 8400 | 4200 | 2100 | 1050 | 525 | 262.5 | 131 |
| 6060 | 235.3 | 1102.5 | 1307.2 | 742.2 | 566.6 | 166.3 | 31.8 | 52.5 |
| 3030 | −63.0 | 788.7 | 1821.5 | 1274.9 | 623.2 | 145.6 | 68.0 | 38.7 |
| 1515 | −107.8 | 18.0 | 1078.4 | 1407.7 | 749.1 | 190.4 | 88.7 | 111.1 |
| 758 | −125.1 | −94.0 | 206.0 | 737.0 | 680.1 | 206.0 | 95.6 | 62.9 |
| 379 | −123.3 | −83.7 | 68.0 | 497.3 | 245.6 | 193.9 | 66.3 | 52.5 |
| 189 | −125.1 | −95.8 | −61.3 | 247.3 | 169.8 | 130.1 | 95.6 | 50.8 |
| 95 | −125.1 | −118.2 | −95.8 | 137.0 | 73.2 | 52.5 | 45.6 | 9.4 |
| 47 | −128.5 | −123.3 | −82.0 | −14.7 | 228.4 | 24.9 | 62.9 | 21.5 |

B. Cholesterol

Figure 9A:
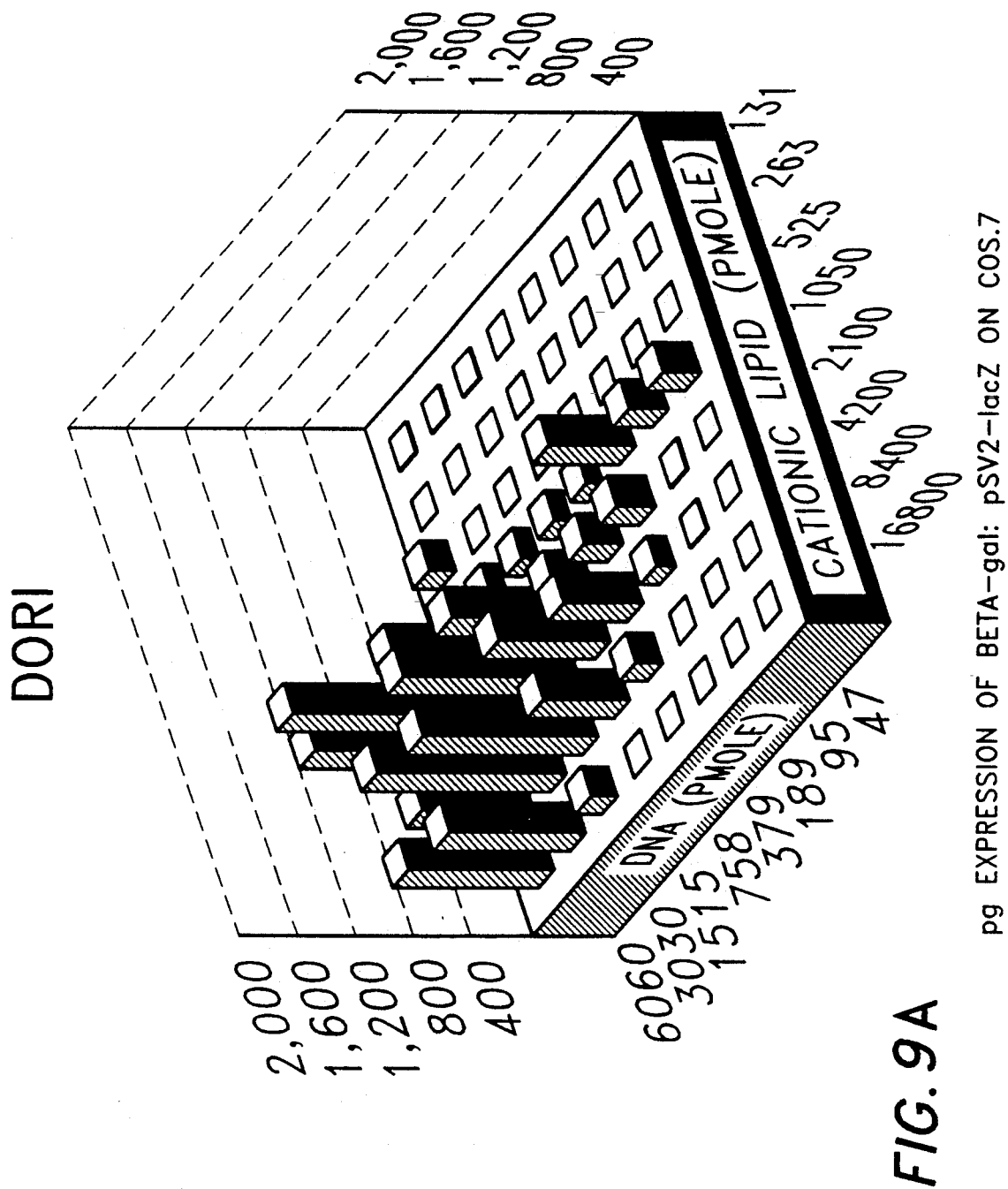
FIGS. 9a–9c demonstrate the effect of cholesterol in the transfection lipid formulation on the efficiency of DNA transfection.
Figure 9B:
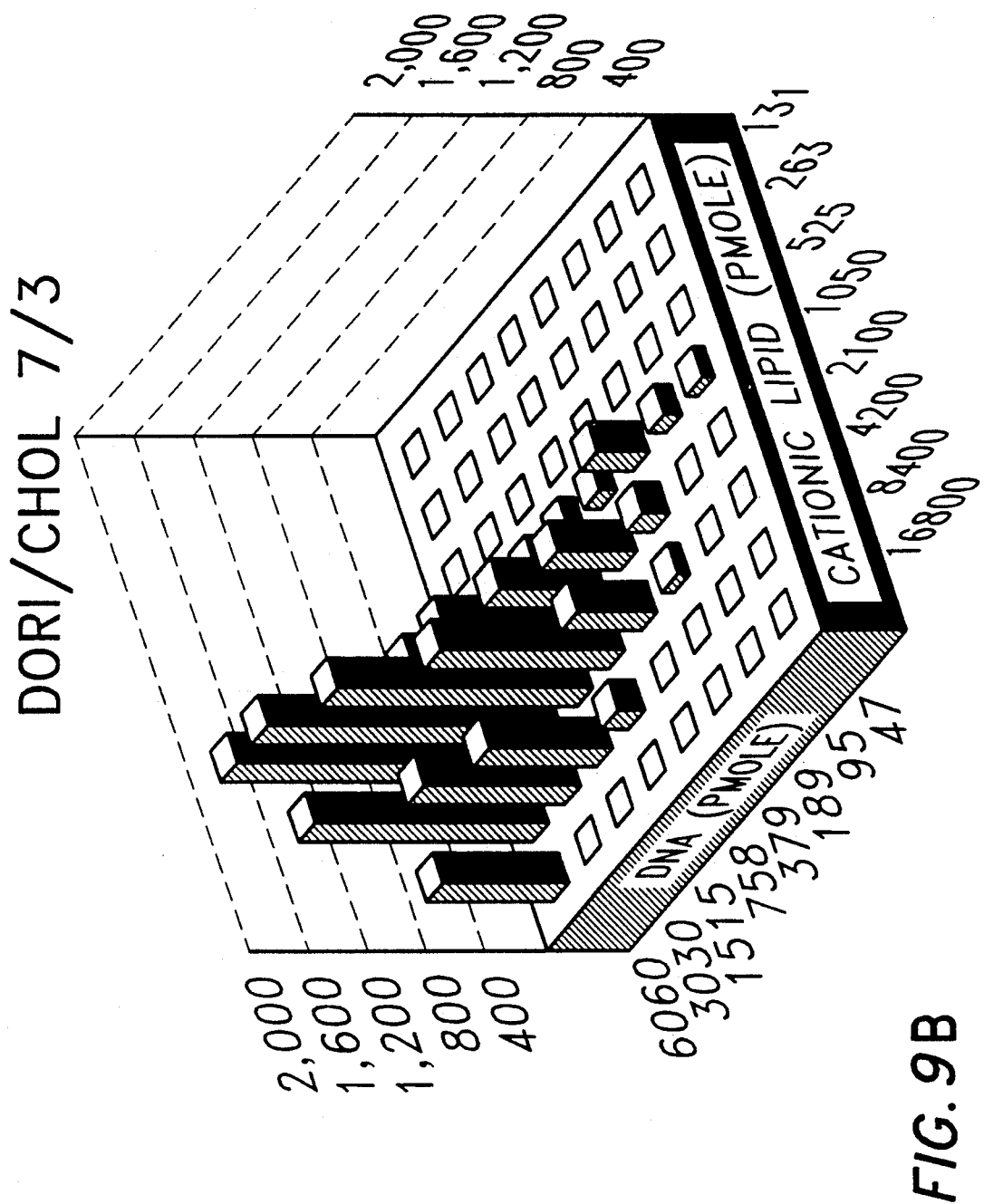
Figure 9C:
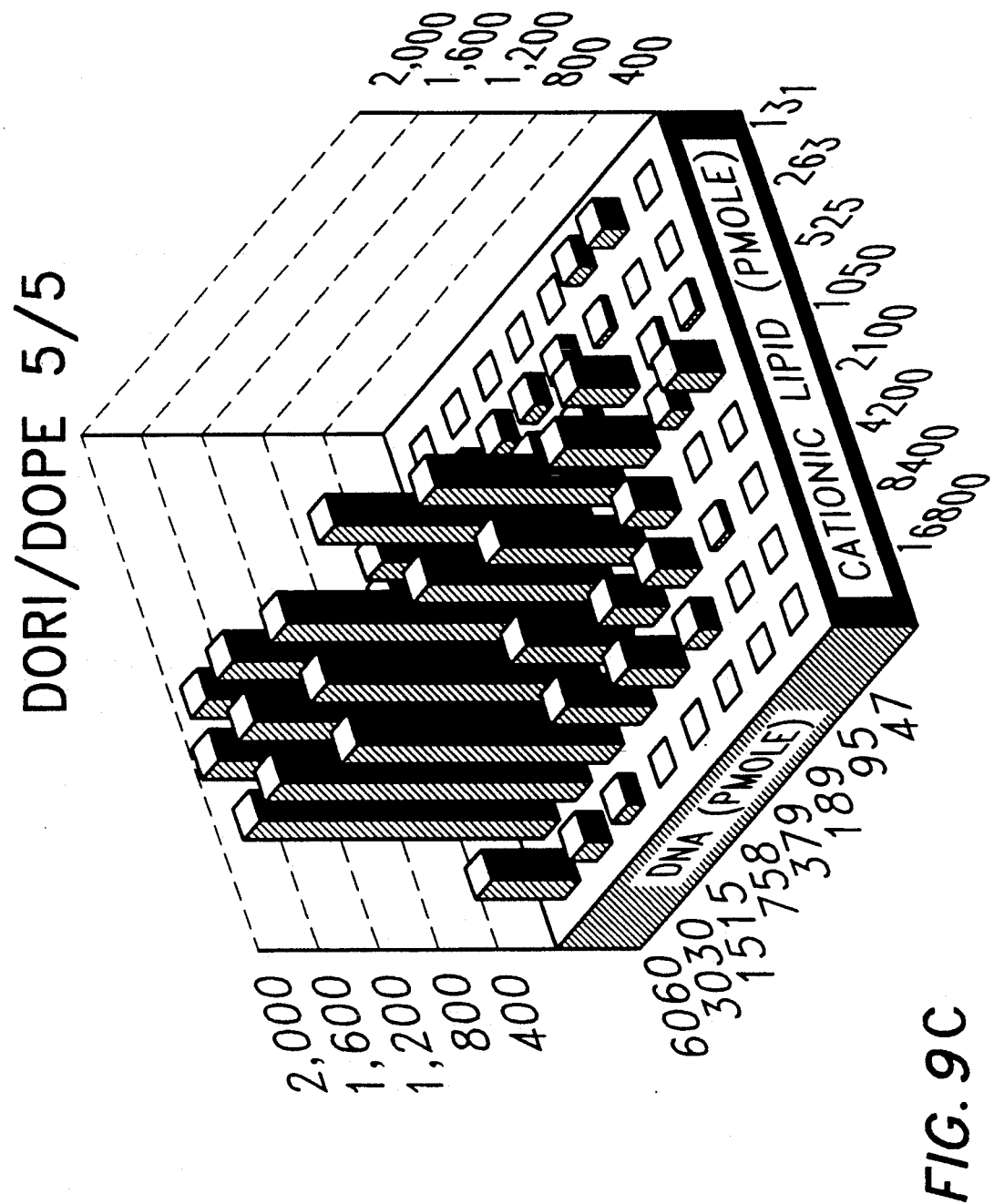

Cholesterol (CHOL) was added to DORI at a molar ratio of DORI/CHOL 7/3 and the lipid formulation used to transfect COS.7 cells at a density of 40,000 cells/well with pSV2-lacZ according to the procedure of Example 14B. The same cells were transfected using DORI/DOPE for a comparative value. The formulation were evaluated for their comparative transfective efficiency by the expression of β-galactosidase activity as indicated in FIG. 9 and the Tables below:

| | DORI/CHOL (10/0) | | | | | | | |
|---|---|---|---|---|---|---|---|---|
| | Cationic lipid (pmole) | | | | | | | |
| DNA (pmole) | 16.8 | 8.4 | 4.2 | 2.1 | 1.05 | 0.53 | 0.26 | 0.13 |
| 6.06 | 864.2 | 622.2 | 1243.8 | 447.6 | 116.4 | 166.1 | 13.2 | 69.3 |
| 3.03 | 721.5 | 1121.5 | 1527.9 | 703.7 | 101.1 | −39.0 | −26.2 | 91.0 |
| 1.52 | 173.8 | 1073.1 | 939.4 | 577.6 | 194.1 | 12.0 | 38.7 | 89.7 |
| 0.76 | −30.1 | 484.6 | 613.2 | 162.3 | 148.3 | 27.3 | −3.3 | −27.5 |
| 0.38 | −45.4 | 180.1 | 327.9 | 175.0 | 116.4 | 17.1 | 47.6 | 19.6 |
| 0.19 | −70.8 | 40.0 | 130.4 | 201.8 | 536.8 | −33.9 | 23.4 | 19.6 |
| 0.095 | −51.7 | −39.0 | 55.3 | 54.0 | 243.8 | −3.3 | −32.6 | −28.8 |
| 0.047 | −109.0 | −75.9 | 20.9 | 10.7 | 186.5 | 15.8 | 23.4 | −37.7 |

| | DORI/CHOL (7/3) | | | | | | | |
|---|---|---|---|---|---|---|---|---|
| | Cationic lipid (pmole) | | | | | | | |
| DNA (pmole) | 16800 | 8400 | 4200 | 2100 | 1050 | 525 | 262.5 | 131 |
| 6060 | 669.0 | 1445.1 | 1810.3 | 680.5 | 55.6 | 0.0 | 0.0 | 0.0 |
| 3030 | 5.7 | 1232.5 | 1784.6 | 723.3 | 89.9 | 0.0 | 0.0 | 0.0 |
| 1515 | 0.0 | 626.2 | 1437.9 | 720.4 | 131.2 | 0.0 | 38.5 | 0.0 |
| 758 | 0.0 | 164.1 | 1047.1 | 547.8 | 141.2 | 0.0 | 0.0 | 0.0 |
| 379 | 0.0 | 0.0 | 319.5 | 342.4 | 101.3 | 0.0 | 0.0 | 0.0 |
| 189 | 0.0 | 0.0 | 71.3 | 138.4 | 302.4 | 0.0 | 0.0 | 0.0 |
| 95 | 0.0 | 0.0 | 37.1 | 0.0 | 117.0 | 0.0 | 0.0 | 0.0 |
| 47 | 0.0 | 0.0 | 0.0 | 0.0 | 64.2 | 0.0 | 0.0 | 0.0 |

| DNA (pmole) | DORI/DOPE (5/5) Cationic lipid (pmole) | | | | | | | |
|---|---|---|---|---|---|---|---|---|
| | 16800 | 8400 | 4200 | 2100 | 1050 | 525 | 262.5 | 131 |
| 6060 | 596.9 | 1858.9 | 2010.5 | 1917.0 | 1283.9 | 445.3 | 273.9 | 0.6 |
| 3030 | 162.0 | 1914.2 | 1936.8 | 1921.2 | 965.2 | 265.4 | 271.1 | 30.3 |
| 1515 | 109.6 | 1624.0 | 1646.5 | 1775.4 | 1109.6 | 462.3 | 91.2 | 34.6 |
| 758 | 11.9 | 598.3 | 722.9 | 1064.3 | 1432.6 | 218.7 | 99.7 | 21.8 |
| 379 | −19.3 | 441.1 | 385.8 | 837.7 | 1077.1 | 486.4 | 237.1 | 20.4 |
| 189 | −85.8 | 145.0 | 356.1 | 333.4 | 582.7 | 391.5 | 85.6 | 150.7 |
| 95 | −151.0 | 40.2 | 78.5 | 21.8 | 210.2 | 54.4 | 33.1 | 170.5 |
| 47 | −173.7 | −26.3 | 10.5 | −34.8 | 292.4 | 79.9 | 11.9 | −67.4 |

There will be various modifications, improvements, and applications of the disclosed invention that will be apparent to those skilled in the art, and the present application is intended to cover such embodiments. Although the present invention has been described in the context of certain preferred embodiments, it is intended that the full scope of the disclosure be measured by reference to the following claims.

What is claimed is:

1. A composition having the structure

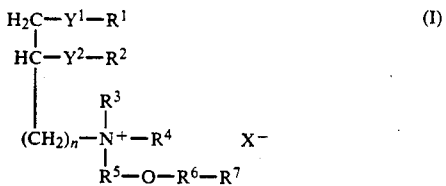

wherein
$Y^1$ and $Y^2$ are the same or different and are, —O—C(O)—, or —O—;
$R^1$ is H, or $C_1$ to $C_{24}$ alkyl or alkenyl;
$R^2$ is $C_1$ to $C_{24}$ alkyl or alkenyl;
$R^3$ and $R^4$ are the same or different and are $C_1$ to $C_{24}$ alkyl, or H;
$R^5$ is $C_1$ to $C_{24}$ alkyl straight chain or branched chain;
$R^6$ is —C(O)—(CH$_2$)$_m$—NH—, a diaminocarboxylate ester group which is alkyl, aryl, or aralkyl, or —C(O)—(CH$_2$)$_m$—NH— linked to said diaminocarboxylate ester group, or is absent;
$R^7$ is H, spermine, spermidine, a histone, or a protein with DNA-binding specificity, or the same groups wherein the amine functionalities of the $R^7$ moiety are quaternized with $R^3$, $R^4$, or $R^5$ groups; or
$R^7$ is an L- or D-alpha amino acid having a positively charged group on the side chain, said amino acids comprising arginine, histidine, lysine or ornithine or analogues thereof, or wherein the amine of the $R^7$ moiety is quaternized with $R^3$, $R^4$ or $R^5$ groups; or
$R^7$ is a polypeptide selected from the group consisting of L-or D-alpha amino acids, wherein at least one of the amino acids residues comprises arginine, histidine, lysine, ornithine, or analogues thereof;
n is 1 to 8;
m is 1 to 18; and
X is a non-toxic anion.

2. A composition according to claim 1 wherein $R^3$ and $R^4$ are individually $C_1$ to $C_{23}$ alkyl groups, $R^5$ is —(CH$_2$)$_m$—, $R^6$ is absent, $R^7$ is H, and $R^1$ and $R^2$ individually have from 0 to 6 sites of unsaturation, and have the structure

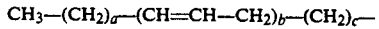

wherein the sum of a and c is from 1 to 23; and b is 0 to 6.

3. A composition according to claim 2, wherein $Y^1$ and $Y^2$ are alike and are —O—C(O)—.

4. A composition according to claim 3, which is DL-1,2-dioleoyl-3-dimethylaminopropyl-β-hydroxyethylammonium and its salts.

5. A composition according to claim 2 wherein $Y^1$ and $Y^2$ are alike and are —O—.

6. A composition according to claim 5, which is 1,2-O-dioleyl-3-dimethylaminopropyl-β-hydroxyethylammonium and its salts.

7. A composition according to claim 2 wherein $Y^1$ and $Y^2$ are different and are either —O— or —O—C(O)—.

8. A composition according to claim 7 which is 1-O-oleyl-2-oleyl-3-dimethylaminopropyl-β-hydroxyethylammonium and its salts.

9. 3,5-(N,N-dilysyl)-diaminobenzoyl-3-(DL-1,2-dioleoyl-dimethylaminopropyl-β-hydroxyethylamine).

10. 3,5-(N,N-dilysyl)-diaminobenzoylglycyl-3-(DL-1,2-dioleoyl-dimethylaminopropyl-β-hydroxyethylamine).

11. L-spermine-5-carboxyl-3-(DL-1,2-dioleoyldimethylaminopropyl-β-hydroxyethylamine).

12. A composition having the structure

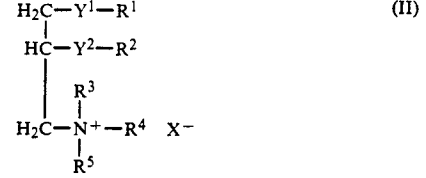

or an optical isomer thereof, wherein
$Y^1$ and $Y^2$ are different and are either, —O—C(O)— or —O—;
$R^1$ is $C_1$ to $C_{24}$ alkyl or alkenyl, or H;
$R^2$ is $C_1$ to $C_{24}$ alkyl or alkenyl;
$R^3$, $R^4$ and $R^5$ are the same or different and are H, $C_1$ to $C_{14}$ alkyl, $C_7$ to $C_{11}$ aryl or alkaryl, or at least two of $R^3$, $R^4$ and
$R^5$ are taken together to form quinuclidino, piperidino, pyrrolidino, or morpholino; and
X is a non-toxic anion.

* * * * *